(12) United States Patent
Aviles et al.

(10) Patent No.: US 11,730,639 B2
(45) Date of Patent: Aug. 22, 2023

(54) WEBS WITH COMPOSITIONS THEREON

(71) Applicant: The Procter & Gamble Company, Cincinnati, OH (US)

(72) Inventors: Misael Omar Aviles, Hamilton, OH (US); Martin Ian James, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1016 days.

(21) Appl. No.: 16/529,816

(22) Filed: Aug. 2, 2019

(65) Prior Publication Data

US 2020/0038263 A1    Feb. 6, 2020

Related U.S. Application Data

(60) Provisional application No. 62/714,104, filed on Aug. 3, 2018.

(51) Int. Cl.
*A61F 13/513* (2006.01)
*A61F 13/512* (2006.01)
(Continued)

(52) U.S. Cl.
CPC ...... *A61F 13/51305* (2013.01); *A61F 13/512* (2013.01); *A61F 13/514* (2013.01);
(Continued)

(58) Field of Classification Search
CPC ................ A61F 13/512; A61F 13/5126; A61F 13/51305
See application file for complete search history.

(56) References Cited

U.S. PATENT DOCUMENTS 1,668,322 A    5/1928   Kessler, Jr.
1,867,314 A    7/1932   Gurwick
(Continued)

FOREIGN PATENT DOCUMENTS

CN         1286605 A      3/2001
CN       104323884 A      2/2015
(Continued)

OTHER PUBLICATIONS

All Office Actions, U.S. Appl. No. 16/529,819.
(Continued)

*Primary Examiner* — Catharine L Anderson
*Assistant Examiner* — Arjuna P Chatrathi
(74) *Attorney, Agent, or Firm* — Amanda Herman Berghauer; George D. Leal

(57) ABSTRACT

A web having a first surface and a second surface, a plurality of apertures extending through the web from the first surface to the second surface, wherein at least a portion of the plurality of apertures are treated with a composition and at least a portion of the apertures are untreated is disclosed. The treated apertures form a plurality of treated aperture zones, and the untreated apertures form a plurality of untreated aperture zones. Each of the plurality of treated aperture zones has one or more apertures, and each of the plurality of untreated aperture zones has one or more apertures. The plurality of treated aperture zones includes between about 25 percent to about 75 percent of the plurality of apertures.

9 Claims, 25 Drawing Sheets

(51) Int. Cl.
   *A61F 13/514* (2006.01)
   *A61F 13/51* (2006.01)
   *A61F 13/536* (2006.01)
   *A61F 13/15* (2006.01)
(52) U.S. Cl.
   CPC ........ *A61F 13/536* (2013.01); *A61F 2013/16* (2013.01); *A61F 2013/51061* (2013.01); *A61F 2013/51066* (2013.01)

(56) References Cited

U.S. PATENT DOCUMENTS

| | | | |
|---|---|---|---|
| 2,226,163 A | 12/1940 | Dufour | |
| 2,427,765 A | 9/1947 | Chollar | |
| 2,468,400 A | 4/1949 | Huebner | |
| 2,864,310 A | 12/1958 | Nelson | |
| 3,055,296 A | 9/1962 | Farrow | |
| 3,056,384 A | 10/1962 | Beale et al. | |
| 3,265,500 A | 8/1966 | Lewis | |
| 3,294,016 A | 12/1966 | Kessler et al. | |
| 3,301,746 A | 1/1967 | Sanford et al. | |
| 3,473,576 A | 10/1969 | Amneus | |
| 3,573,164 A | 3/1971 | Friedberg et al. | |
| 3,738,269 A | 6/1973 | Wagner | |
| 3,759,261 A | 9/1973 | Wang | |
| 3,821,068 A | 6/1974 | Shaw | |
| 3,896,722 A | 7/1975 | Farrow | |
| 3,896,723 A | 7/1975 | Farrow et al. | |
| 3,974,025 A | 8/1976 | Ayers | |
| 3,994,771 A | 11/1976 | Morgan, Jr. et al. | |
| 4,033,258 A | 7/1977 | Farrow | |
| 4,041,951 A | 8/1977 | Sanford | |
| 4,098,630 A | 7/1978 | Morse | |
| 4,191,609 A | 3/1980 | Trokhan | |
| 4,191,756 A | 3/1980 | Masi et al. | |
| 4,231,370 A | 11/1980 | Mroz et al. | |
| 4,239,065 A | 12/1980 | Trokhan | |
| 4,243,446 A | 1/1981 | Mathey | |
| 4,275,105 A | 6/1981 | Boyd et al. | |
| 4,300,981 A | 11/1981 | Carstens | |
| 4,333,979 A | 6/1982 | Sciaraffa et al. | |
| 4,355,066 A | 10/1982 | Newman | |
| 4,361,089 A | 11/1982 | Wittkopf et al. | |
| 4,437,408 A | 3/1984 | Arkans | |
| 4,440,597 A | 4/1984 | Wells et al. | |
| 4,452,141 A | 6/1984 | Mistyurik | |
| 4,458,399 A | 7/1984 | Kessler | |
| 4,483,053 A | 11/1984 | Hamisch, Jr. | |
| 4,526,098 A | 7/1985 | Bachman | |
| 4,528,239 A | 7/1985 | Trokhan | |
| 4,529,480 A | 7/1985 | Trokhan | |
| 4,534,094 A | 8/1985 | Kessler | |
| 4,550,681 A | 11/1985 | Zimmer et al. | |
| 4,574,732 A | 3/1986 | Verwey et al. | |
| 4,599,627 A | 7/1986 | Vollert | |
| 4,637,859 A | 1/1987 | Trokhan | |
| 4,738,674 A | 4/1988 | Todd et al. | |
| 4,766,840 A | 8/1988 | Beckley et al. | |
| 4,812,899 A | 3/1989 | Kueppers | |
| 4,844,952 A | 7/1989 | Korenkiewicz et al. | |
| 4,846,821 A | 7/1989 | Lyons et al. | |
| 4,878,977 A | 11/1989 | Kueppers | |
| 4,909,879 A | 3/1990 | Ball | |
| 4,939,992 A | 7/1990 | Bird | |
| 5,082,703 A | 1/1992 | Longobardi | |
| 5,161,829 A | 11/1992 | Detrick et al. | |
| 5,282,419 A | 2/1994 | Barrois | |
| 5,288,348 A | 2/1994 | Modrak | |
| 5,316,582 A | 5/1994 | Dubel | |
| 5,332,613 A | 7/1994 | Taylor et al. | |
| 5,354,289 A | 10/1994 | Mitchell et al. | |
| 5,364,504 A | 11/1994 | Smurkoski et al. | |
| 5,417,789 A | 5/1995 | Lauilzen | |
| 5,429,686 A | 7/1995 | Chiu et al. | |
| 5,458,590 A | 10/1995 | Schleinz et al. | |
| 5,470,640 A | 11/1995 | Modrak | |
| 5,503,076 A | 4/1996 | Yeo | |
| 5,529,664 A | 6/1996 | Trokhan et al. | |
| 5,549,790 A | 8/1996 | Van Phan | |
| 5,556,509 A | 9/1996 | Trokhan et al. | |
| 5,580,423 A | 12/1996 | Ampulski et al. | |
| 5,609,725 A | 3/1997 | Van Phan | |
| 5,629,052 A | 5/1997 | Trokhan et al. | |
| 5,637,194 A | 6/1997 | Ampulski et al. | |
| 5,672,248 A | 9/1997 | Wendt et al. | |
| 5,674,663 A | 10/1997 | McFarland et al. | |
| 5,679,222 A | 10/1997 | Rasch et al. | |
| 5,693,187 A | 12/1997 | Ampulski et al. | |
| 5,695,855 A | 12/1997 | Yeo et al. | |
| 5,705,011 A | 1/1998 | Bodford et al. | |
| 5,709,775 A | 1/1998 | Trokhan et al. | |
| 5,714,041 A | 2/1998 | Ayers et al. | |
| 5,733,634 A | 3/1998 | Karel | |
| 5,734,800 A | 3/1998 | Herbert et al. | |
| 5,766,389 A | 6/1998 | Brandon et al. | |
| 5,776,307 A | 7/1998 | Ampulski et al. | |
| 5,785,697 A | 7/1998 | Trombetta et al. | |
| 5,795,440 A | 8/1998 | Ampulski et al. | |
| 5,814,190 A | 9/1998 | Van Phan | |
| 5,817,377 A | 10/1998 | Trokhan et al. | |
| 5,846,379 A | 12/1998 | Ampulski et al. | |
| 5,855,739 A | 1/1999 | Ampulski et al. | |
| 5,858,514 A | 1/1999 | Bowers | |
| 5,861,082 A | 1/1999 | Ampulski et al. | |
| 5,865,950 A | 2/1999 | Vinson et al. | |
| 5,871,887 A | 2/1999 | Trokhan et al. | |
| 5,897,745 A | 4/1999 | Ampulski et al. | |
| 5,900,109 A | 5/1999 | Sanders et al. | |
| 5,904,811 A | 5/1999 | Ampulski et al. | |
| 5,906,161 A | 5/1999 | Kessler | |
| 5,906,710 A | 5/1999 | Trokhan | |
| 5,942,085 A | 8/1999 | Neal et al. | |
| 5,972,477 A | 10/1999 | Kim et al. | |
| 5,990,377 A | 11/1999 | Chen | |
| 6,033,513 A | 3/2000 | Nakamura | |
| 6,048,938 A | 4/2000 | Neal et al. | |
| 6,096,412 A | 8/2000 | McFarland et al. | |
| 6,120,488 A | 9/2000 | Vanrijswijck et al. | |
| 6,127,595 A | 10/2000 | Makoui et al. | |
| 6,129,477 A | 10/2000 | Shoykhet | |
| 6,173,646 B1 | 1/2001 | Tanaka et al. | |
| 6,187,138 B1 | 2/2001 | Neal et al. | |
| 6,234,078 B1 | 5/2001 | Kessler | |
| 6,281,269 B1 | 8/2001 | Schut | |
| 6,284,942 B1 | 9/2001 | Rabin | |
| 6,307,119 B1 | 10/2001 | Cammarota et al. | |
| 6,322,665 B1 | 11/2001 | Sun et al. | |
| 6,330,857 B1 | 12/2001 | Maximovsky et al. | |
| 6,350,711 B1 | 2/2002 | Potts | |
| 6,403,857 B1 | 6/2002 | Gross et al. | |
| 6,458,211 B1 | 10/2002 | Wefers et al. | |
| 6,477,948 B1 | 11/2002 | Nissing et al. | |
| 6,531,027 B1 | 3/2003 | Lender et al. | |
| 6,572,575 B1 | 6/2003 | Shimada et al. | |
| 6,610,131 B2 | 8/2003 | Harris et al. | |
| 6,624,100 B1 | 9/2003 | Pike | |
| 6,627,022 B2 | 9/2003 | Fusco | |
| 6,651,560 B2 | 11/2003 | Neuhaus | |
| 6,993,964 B2 | 2/2006 | Franz et al. | |
| 7,306,699 B2 * | 12/2007 | Urlaub .................. D21H 27/00 | |
| | | | 162/134 |
| 7,611,582 B2 | 11/2009 | McNeil et al. | |
| 7,648,752 B2 | 1/2010 | Hoying et al. | |
| 7,703,394 B2 | 4/2010 | Neuhaus | |
| 7,736,688 B2 | 6/2010 | Oetjen et al. | |
| 7,816,285 B2 | 10/2010 | MacDonald et al. | |
| 8,012,297 B2 | 9/2011 | Baldauf | |
| 8,153,226 B2 | 4/2012 | Curro et al. | |
| 8,158,253 B2 | 4/2012 | Spinks | |
| 8,163,132 B2 | 4/2012 | Kien | |
| 8,691,041 B2 | 4/2014 | Oetjen | |
| 8,943,957 B2 | 2/2015 | McNeil et al. | |
| 8,945,334 B2 | 2/2015 | Oetjen | |
| 9,050,220 B2 | 6/2015 | Digiacomantonio et al. | |

(56) References Cited

U.S. PATENT DOCUMENTS

| | | |
|---|---|---|
| 9,102,182 B2 | 8/2015 | McNeil et al. |
| 9,237,973 B2 | 1/2016 | Abuto |
| 9,414,971 B2 | 8/2016 | Oetjen |
| 9,579,924 B2 | 2/2017 | Boegli |
| 9,610,200 B2 | 4/2017 | Oetjen |
| 9,642,752 B2 | 5/2017 | Oetjen |
| 9,707,133 B2 | 7/2017 | Digiacomantonio et al. |
| 2001/0044611 A1 | 11/2001 | Noda et al. |
| 2002/0002358 A1 | 1/2002 | Durrance et al. |
| 2002/0058056 A1 | 5/2002 | Yahiaoui et al. |
| 2002/0087129 A1 | 7/2002 | Di Luccio et al. |
| 2002/0112832 A1 | 8/2002 | Burazin et al. |
| 2002/0138054 A1 | 9/2002 | Erdman |
| 2002/0143304 A1 | 10/2002 | Elder |
| 2002/0193765 A1 | 12/2002 | Kudo |
| 2003/0050618 A1 | 3/2003 | Kondo |
| 2003/0065299 A1 | 4/2003 | Carlucci et al. |
| 2003/0114818 A1 | 6/2003 | Benecke et al. |
| 2003/0124311 A1 | 7/2003 | Cree |
| 2003/0171729 A1 | 9/2003 | Kaun et al. |
| 2003/0194481 A1 | 10/2003 | Lippelt |
| 2004/0102750 A1* | 5/2004 | Jameson ............... A61F 13/511 604/367 |
| 2004/0122386 A1 | 6/2004 | Mocadlo |
| 2004/0127872 A1 | 7/2004 | Petryk |
| 2004/0170813 A1 | 9/2004 | Digiacomantonio et al. |
| 2004/0176736 A1 | 9/2004 | Christon et al. |
| 2005/0177123 A1 | 8/2005 | Catalan |
| 2005/0281976 A1 | 12/2005 | Curro et al. |
| 2006/0008514 A1 | 1/2006 | Koenig et al. |
| 2006/0135920 A1 | 6/2006 | Virgilio et al. |
| 2006/0201630 A1 | 9/2006 | Puffe et al. |
| 2007/0026209 A1 | 2/2007 | MacDonald et al. |
| 2007/0049153 A1 | 3/2007 | Dunbar et al. |
| 2007/0093770 A1* | 4/2007 | Ecker ................. A61F 13/4758 604/385.01 |
| 2008/0036196 A1 | 2/2008 | Steenblik et al. |
| 2008/0132872 A1 | 6/2008 | Trennepohl et al. |
| 2010/0036352 A1 | 2/2010 | Hood et al. |
| 2010/0126366 A1 | 5/2010 | Kasper et al. |
| 2010/0206221 A1 | 8/2010 | Branca et al. |
| 2010/0209664 A1 | 8/2010 | Sato et al. |
| 2010/0222757 A1 | 9/2010 | Tee, Jr. |
| 2010/0233438 A1 | 9/2010 | Stone et al. |
| 2011/0106035 A1 | 5/2011 | Arora et al. |
| 2011/0112499 A1 | 5/2011 | Trennepohl et al. |
| 2011/0302733 A1 | 12/2011 | Yuan |
| 2012/0222568 A1 | 9/2012 | Byrne et al. |
| 2012/0296303 A1* | 11/2012 | Ng .................. A61F 13/51305 604/378 |
| 2013/0197462 A1* | 8/2013 | Abuto ............... A61F 13/51305 604/378 |
| 2014/0121621 A1 | 5/2014 | Kirby et al. |
| 2014/0180232 A1 | 6/2014 | Gagliardi et al. |
| 2014/0234575 A1 | 8/2014 | Mitsuno et al. |
| 2014/0296814 A1 | 10/2014 | Gray et al. |
| 2014/0324009 A1 | 10/2014 | Lee |
| 2015/0038933 A1 | 2/2015 | Day |
| 2015/0173964 A1 | 6/2015 | Coe et al. |
| 2015/0250662 A1 | 9/2015 | Isele et al. |
| 2015/0282997 A1 | 10/2015 | Arizti |
| 2015/0284892 A1 | 10/2015 | Galie et al. |
| 2015/0343480 A1 | 12/2015 | Byrne et al. |
| 2016/0067118 A1* | 3/2016 | Hammons ............ A61F 13/5123 428/137 |
| 2016/0074251 A1 | 3/2016 | Strube et al. |
| 2016/0074252 A1 | 3/2016 | Strube et al. |
| 2016/0074253 A1 | 3/2016 | Strube et al. |
| 2016/0074254 A1 | 3/2016 | Orr et al. |
| 2016/0074255 A1 | 3/2016 | Strube et al. |
| 2016/0074256 A1 | 3/2016 | Strube et al. |
| 2016/0075122 A1 | 3/2016 | Strube et al. |
| 2016/0075123 A1 | 3/2016 | Strube et al. |
| 2016/0076180 A1 | 3/2016 | Strube et al. |
| 2016/0076181 A1 | 3/2016 | Strube et al. |
| 2016/0076182 A1 | 3/2016 | Strube et al. |
| 2016/0076184 A1 | 3/2016 | Orr et al. |
| 2016/0129661 A1 | 5/2016 | Arora |
| 2016/0331596 A1 | 11/2016 | Oetjen |
| 2017/0119591 A1 | 5/2017 | Noel |
| 2017/0120260 A1 | 5/2017 | Oetjen |
| 2017/0210110 A1 | 7/2017 | Oetjen |
| 2017/0225449 A1 | 8/2017 | Aviles |
| 2017/0258650 A1 | 9/2017 | Rosati et al. |
| 2017/0258651 A1* | 9/2017 | Hammons ............ A61F 13/538 |
| 2017/0259524 A1 | 9/2017 | Neton et al. |
| 2017/0259550 A1 | 9/2017 | Neton et al. |
| 2018/0071151 A1 | 3/2018 | Aviles |
| 2019/0110939 A1 | 4/2019 | Hammons et al. |
| 2020/0038262 A1 | 2/2020 | Aviles et al. |

FOREIGN PATENT DOCUMENTS

| | | |
|---|---|---|
| CN | 104975365 A | 10/2015 |
| DE | 19854634 C1 | 2/2000 |
| EP | 0165807 A1 | 12/1985 |
| EP | 0951889 A1 | 10/1999 |
| EP | 1338262 A1 | 8/2003 |
| EP | 1527898 A1 | 5/2005 |
| EP | 1075948 B1 | 11/2005 |
| EP | 0959842 B2 | 6/2006 |
| EP | 1673225 B1 | 8/2008 |
| EP | 2745823 A1 | 6/2014 |
| GB | 1176321 | 1/1970 |
| GB | 1241793 | 8/1971 |
| GB | 1241794 | 8/1971 |
| GB | 1350059 | 4/1974 |
| GB | 1396282 | 6/1975 |
| GB | 1439458 | 6/1976 |
| GB | 1468360 | 3/1977 |
| GB | 1570545 | 7/1980 |
| GB | 2314292 A1 | 12/1997 |
| WO | WO8400516 A1 | 2/1984 |
| WO | WO9954143 A1 | 10/1999 |
| WO | WO03020835 A1 | 3/2003 |
| WO | WO2007070132 A1 | 6/2007 |
| WO | WO2008103650 A2 | 8/2008 |
| WO | WO2009062998 A1 | 5/2009 |
| WO | WO2010071543 A1 | 6/2010 |
| WO | WO2012176656 A1 | 12/2012 |

OTHER PUBLICATIONS

International Search Report and Written Opinion for PCT/US2016/059242 dated Feb. 15, 2017.

Search Report and Written Opinion for PCT/US2017/016324 dated May 30, 2017.

International Search Report for PCT/US2017/021485 dated May 18, 2017.

Search Report and Written Opinion for PCT/US2017/050603 dated Nov. 7, 2017.

PCT Search Report and Written Opinion dated Aug. 2, 2019.

Hatch, Kathryn, "Nonwoven Fabrics Structures", Textile Science, 1993, p. 363.

All Office Actions for U.S. Appl. No. 15/698,709, filed Sep. 8, 2017.

* cited by examiner

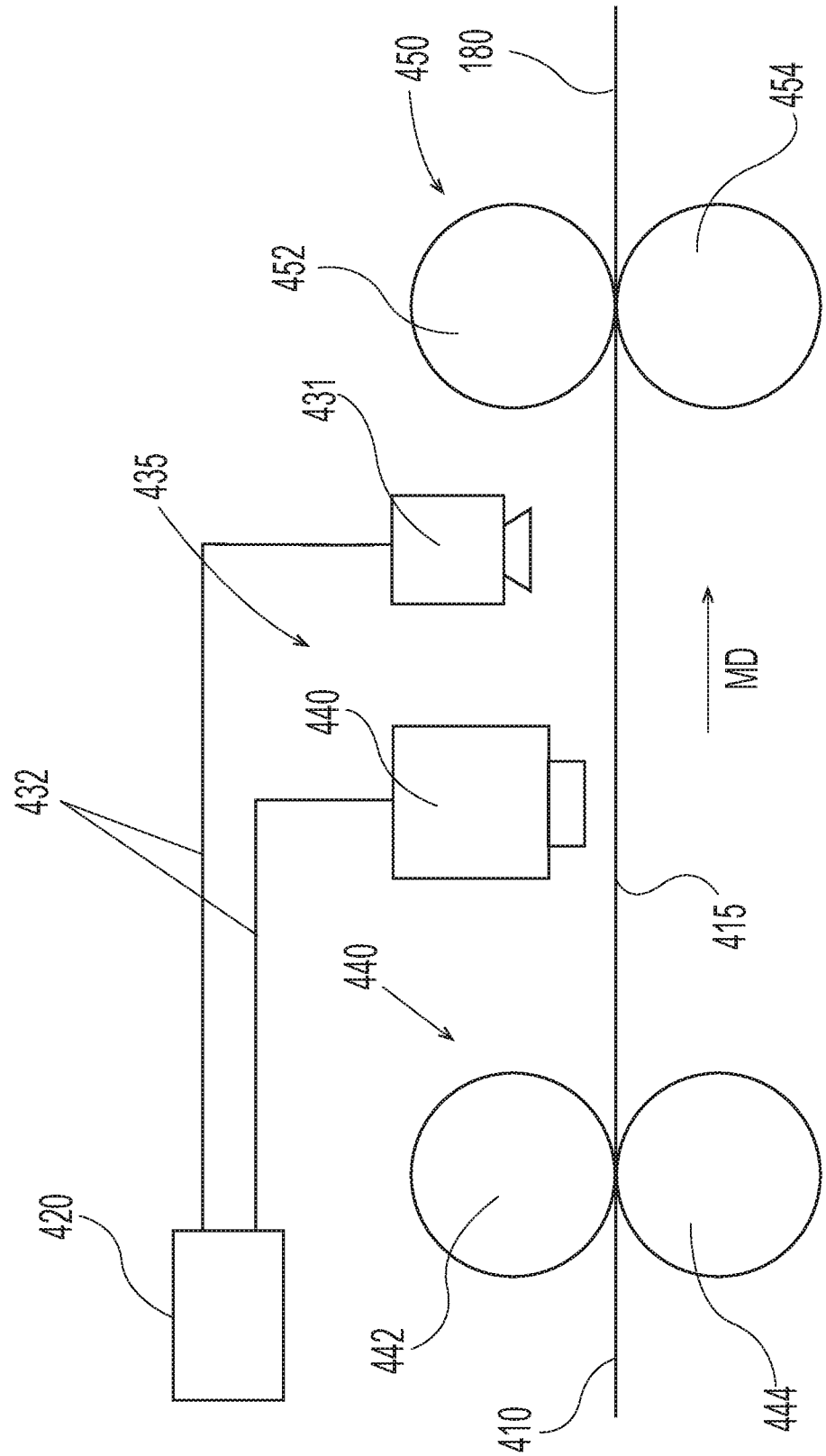

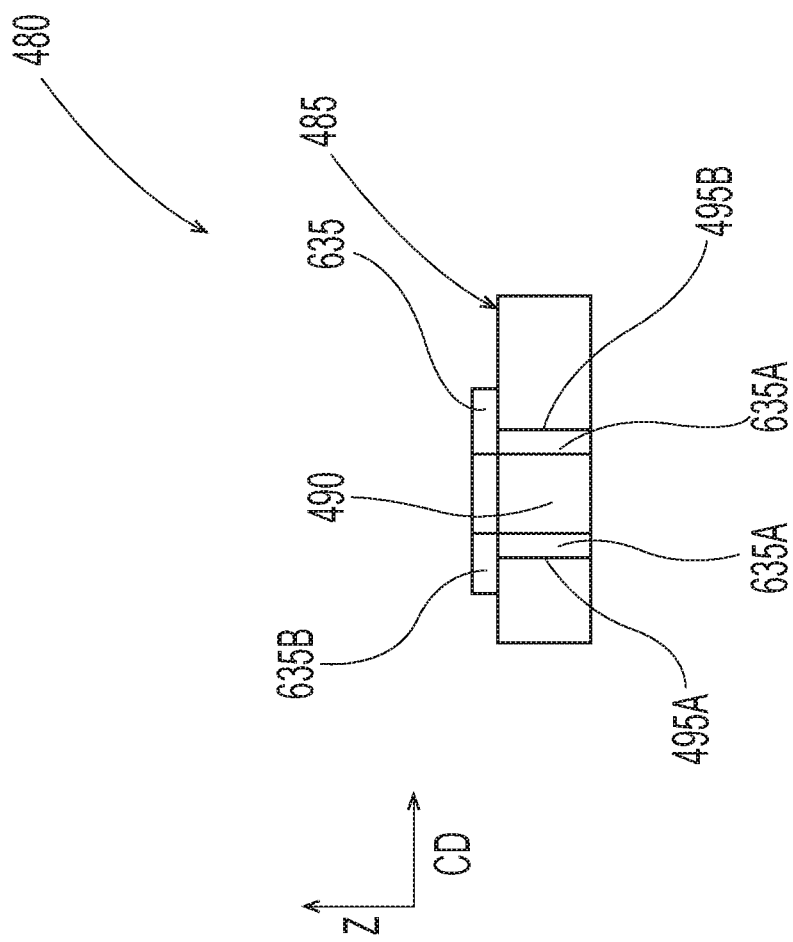

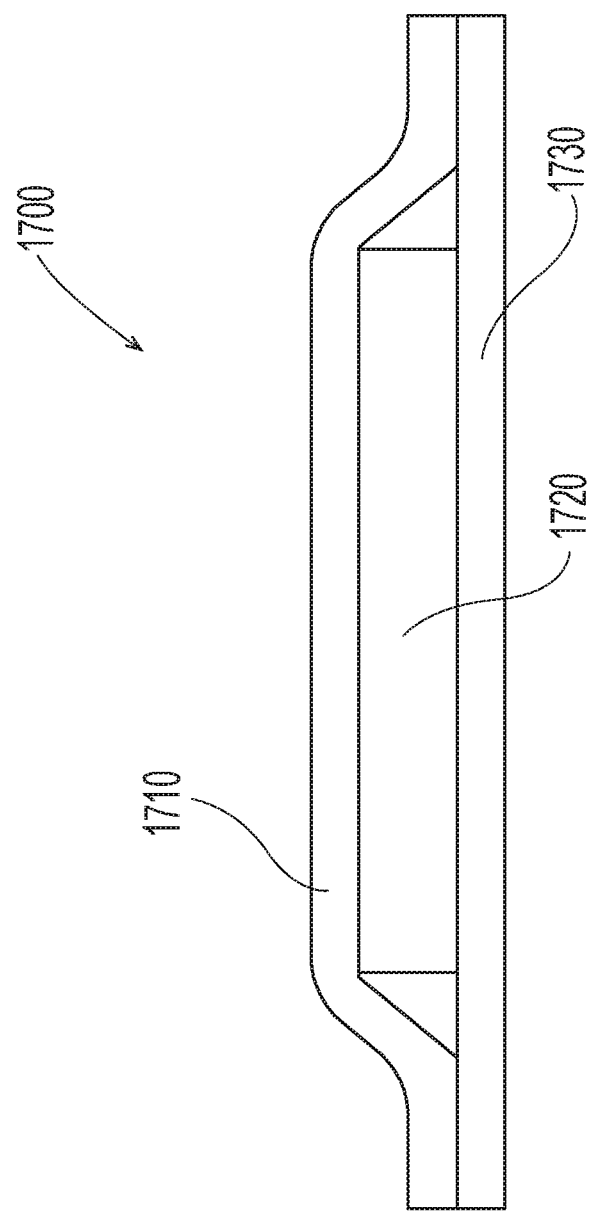

WEBS WITH COMPOSITIONS THEREON

FIELD OF THE INVENTION

The present invention pertains to webs having compositions thereon and methods of depositing compositions.

BACKGROUND OF THE INVENTION

Nonwovens, films, and laminates thereof are widely used in disposable absorbent article manufacturing. For example, many commercially available disposable absorbent articles utilize a nonwoven topsheet and some may use a nonwoven/film laminate backsheet.

The function of the topsheet of a disposable absorbent article can be condensed into two specific performance attributes. First, the topsheet desirably acquires liquid insults in a reasonable time. This can cut down on the wet feeling that can be provided to the user. Second, acquired liquid insults, once drained from the topsheet, desirably should be discouraged from rewetting the topsheet when pressure is applied to the absorbent article. Unfortunately, these performance attributes are often at odds with each other. While some topsheets can acquire liquid insults rapidly, they may perform poorly in the context of rewet. Or conversely, some topsheets may provide outstanding rewet performance but lack in fluid insult acquisition.

Some suggestions for improvement of topsheets include topical coatings. While topical coatings—particularly hydrophilic coatings—can greatly increase the performance of the topsheet in the way of acquisition speed, these coating can detrimentally impact rewet performance. Conversely, hydrophobic coatings have also been suggested to improve topsheet performance. However, hydrophobic coating while greatly improving the rewet performance of the topsheet can detrimentally impact the acquisition speed of the topsheet.

Additionally, application of these coating can increase the cost of production of an absorbent article. Coating equipment while not overly complex, can apply too much of the coating which can lead to the detrimental impact described as well as increased cost due to the amount of coating being deposited. Other suggestions have been to brush the coating on by hand, which also increases the cost of production of absorbent articles. This is particularly true where the coating is applied to discrete features. Namely, such features may be difficult to detect via automated systems which will increase the cost of the application of the coating.

Based on the foregoing, there is a need for a material which can achieve both good acquisition speed and good rewet performance and a method of producing such materials as well as a method for the application of the material thereto.

SUMMARY OF THE INVENTION

The present invention provides webs having a composition or a plurality of compositions thereon. The present invention also provides systems and methods for providing compositions to the web. In one specific example, a web comprises a first surface and a second surface; a plurality of apertures extending through the web from the first surface to the second surface, wherein at least a portion of the plurality of apertures are treated with a composition and at least a portion of the apertures are untreated, wherein the treated apertures form a plurality of treated aperture zones and wherein the untreated apertures form a plurality of untreated aperture zones, wherein each of the plurality of treated aperture zones comprise one or more apertures and wherein each of the plurality of untreated aperture zones comprise one or more apertures, and wherein the plurality of treated aperture zones comprises between about 25 percent to about 75 percent of the plurality of apertures.

In another specific example, a disposable absorbent article comprises a longitudinal centerline and a lateral centerline; a topsheet having a plurality of apertures, the plurality of apertures being arranged in a target zone, and a pair of outer zones, wherein between about 12 percent to about 75 percent of the plurality of apertures in the target zone are treated and at least a portion of the plurality of apertures in the outer zone are untreated; a backsheet attached to the topsheet; and an absorbent core disposed between the topsheet and the backsheet.

BRIEF DESCRIPTION OF THE DRAWINGS

FIG. 5 is a schematic diagram showing another process in accordance with the present disclosure.

FIG. 6 is an exemplary cross section of the web shown in FIG. 4C constructed in accordance with the present disclosure.

FIG. 9 is a schematic representation of a cross section of a disposable absorbent article constructed in accordance with the present disclosure.

DETAILED DESCRIPTION OF THE INVENTION

Figure 1A:
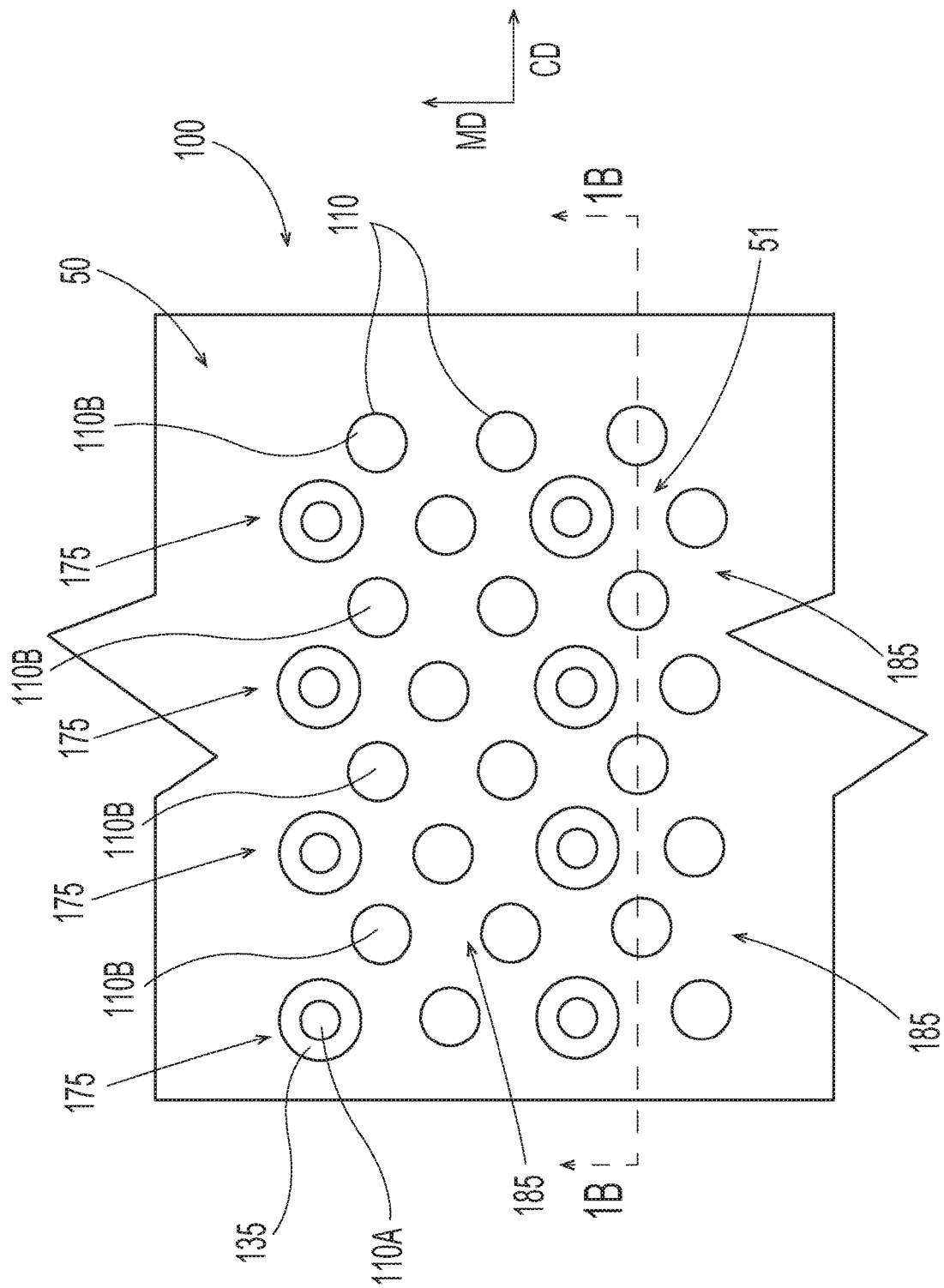
FIG. 1A is a plan view showing a web comprising apertures, a portion of which are treated and a portion of which are untreated in accordance with the present disclosure.

As used herein "hydrophilic" and "hydrophobic" have meanings as well established in the art with respect to the contact angle of a referenced liquid on the surface of a material. Thus, a material having a liquid contact angle of greater than about 90 degrees is considered hydrophobic, and a material having a liquid contact angle of less than about 90 degrees is considered hydrophilic. Compositions which are hydrophobic, will increase the contact angle of a referenced liquid on the surface of a material while compositions which are hydrophilic will decrease the contact angle of a referenced liquid on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein the term "print file" shall mean any streamed or batched electronic sequence provided to a printer such that all required rendering and formatting has been completed sufficient to allow the printer to execute a print pattern without further prerequisite processing or rendering. Various printers may require that the sequence be provided in specific formats. The sequences may have proprietary layers for either the protocols or the physical layers. Common examples include USB, USB 3.0, USB 3.1, Ethernet 10/100, Ethernet IP, GigE, CameraLink, Coax-Express, LVDS, TTL, RS485, RS422, and Serial Comm.; however, the printer may require its own unique protocols instead of industry common protocols.

The webs of the present invention comprise a plurality of apertures. At least a portion of the apertures are treated with a composition and at least another portion of the apertures are untreated. The webs of the present invention may comprise a nonwoven, a film, or laminates thereof. The composition renders the constituent material of the web more hydrophilic than it would be without the composition. The composition may be applied to the web by any suitable method as described herein.

Additionally, the webs of the present disclosure may be utilized in a myriad of disposable absorbent articles. Some examples of disposable absorbent articles, include but are not limited to, feminine pads, sanitary pads, adult incontinence pads, adult incontinence pants, diapers, training pants, and the like. Reference herein may be made specifically to feminine pads or sanitary pads, but such references are utilized for ease of discussion. These terms should include other forms of disposable absorbent articles mentioned herein unless otherwise expressly provided.

Figure 1B:
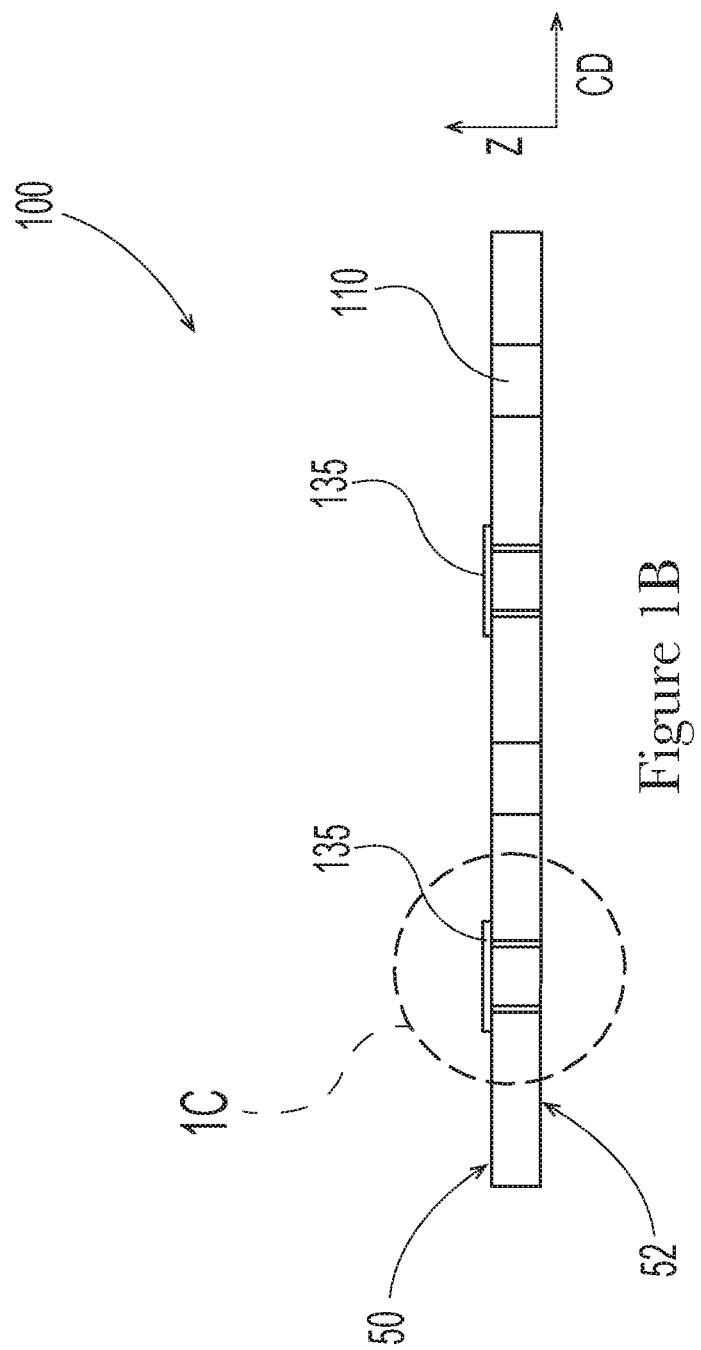
FIG. 1B is a cross-sectional view showing the web of FIG. 1A along line 1B-1B.

As shown in FIGS. 1A and 1B, a web 100 constructed in accordance with the present disclosure is shown. The web 100 comprises a plurality of apertures 110. As shown the apertures 110 may be arranged in staggered rows. However, any suitable aperture configuration may be utilized. For example, in some forms, the apertures 110 may be arranged in patterns and have variable sizes as described in U.S. Patent Application Publication No. 2016/0129661.

In between adjacent apertures 110, land areas 51 are disposed. The land areas 51 are disposed between adjacent treated apertures 110A, adjacent untreated apertures 110B and adjacent treated and untreated apertures. For those forms where composition is provided on a first surface 50 of the web 100, the land areas 51 may not overlap a composition 135 on the first surface. In some forms, the land areas 51 may overlap to a minor extent the composition 135.

The web 100 comprises the first surface 50 and a second surface 52. The apertures 110 extend from the first surface 50 through the second surface 52 of the web 100. The web 100 further comprises a machine direction, denoted as "MD" and a cross machine direction, denoted as "CD." A Z-direction is generally parallel with a thickness of the web 100.

Figure 1C:
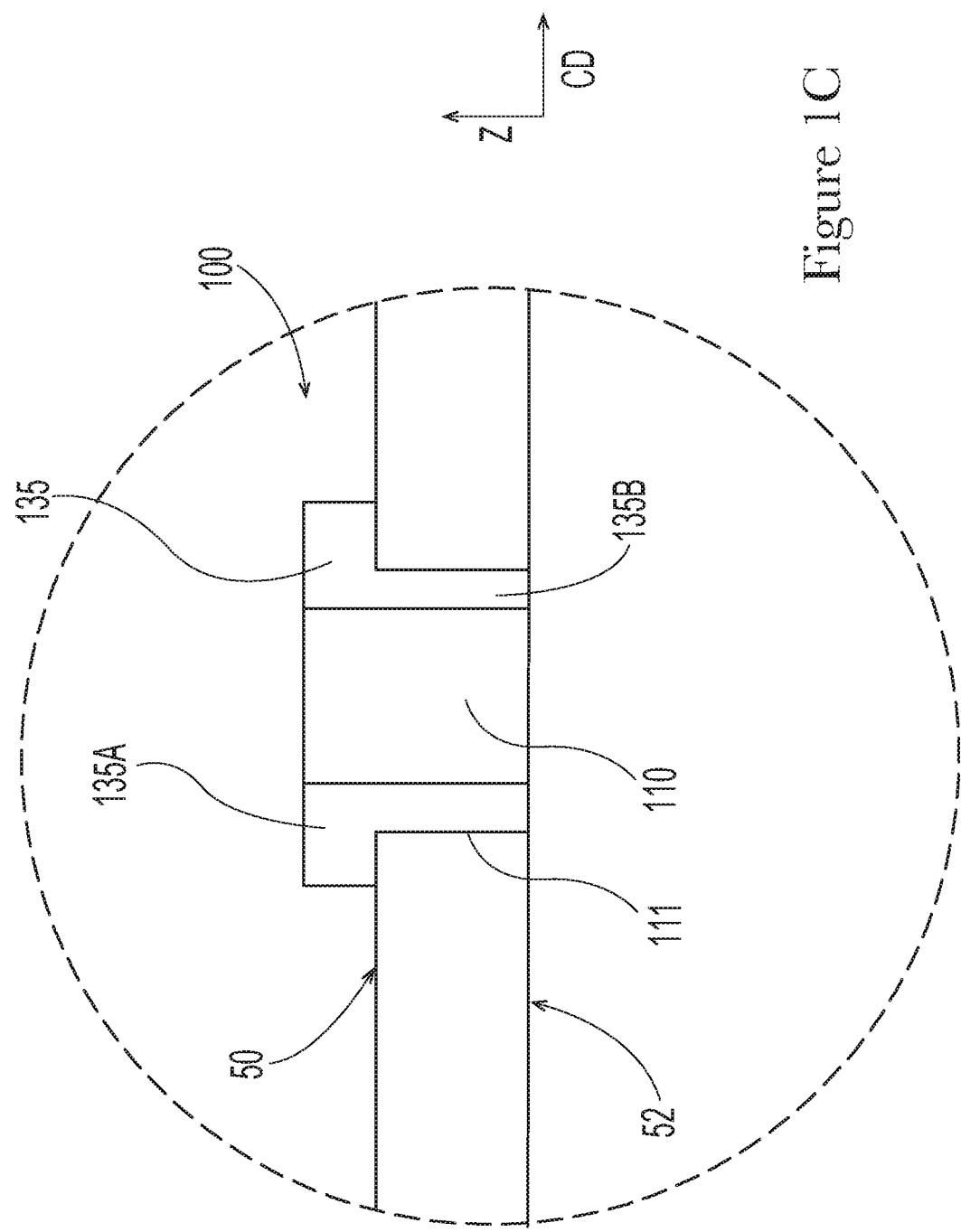
FIG. 1C is a close up view showing the web in cross section from FIG. 1B.

As noted above, at least a portion of the plurality of apertures 110 comprise a composition 135. The application of composition 135 to the web 100 is exaggerated in FIGS. 1A-1C for ease of visualization. As shown in FIG. 1C, the composition 135 may be provided to each of the treated apertures 110 such that a portion of the first surface 50 adjacent the aperture 110 comprises a top composition portion 135A. Additionally, composition 135 may be provided to sidewalls 111 of the aperture 110 in a sidewall composition portion 135B. In some forms, the top composition portion 135A can be provided sans the sidewall composition portion 135B or vice versa. Typically, the top composition portion 135A can extend between about 0.2 mm to about 5 mm beyond the edge of the treated aperture, from about 0.5 to about 3 mm, or from about 0.6 to about 2 mm, specifically reciting all values within these ranges and any ranges created thereby.

Referring back to FIG. 1A, the web 100 comprises a portion of the plurality of apertures which are treated 110A with composition and a portion of the plurality of apertures which are untreated 110B. The plurality of treated apertures 110A may form treated aperture zones 175, and the plurality of untreated apertures may form untreated aperture zones 185. As shown in FIG. 1A, the treated apertures zones comprise at least one treated aperture 110A. However, because an untreated aperture 110B is generally positioned in between adjacent treated apertures 110A each of the treated aperture zones 175 comprise only one treated aperture 110A each.

Still referring to FIG. 1A, the untreated aperture zones 185—as shown, in contrast to the treated aperture zones 175 of FIG. 1A—may comprise one or more untreated apertures 110B per zone. As shown, while some treated apertures 110A are generally disposed between untreated apertures 110B, many adjacent untreated apertures 110B are not separated by a treated aperture 110A. Additional configurations for the treated aperture zones 175 and untreated aperture zones 185 are provided with regard to FIGS. 2A-2C.

Figure 1D:
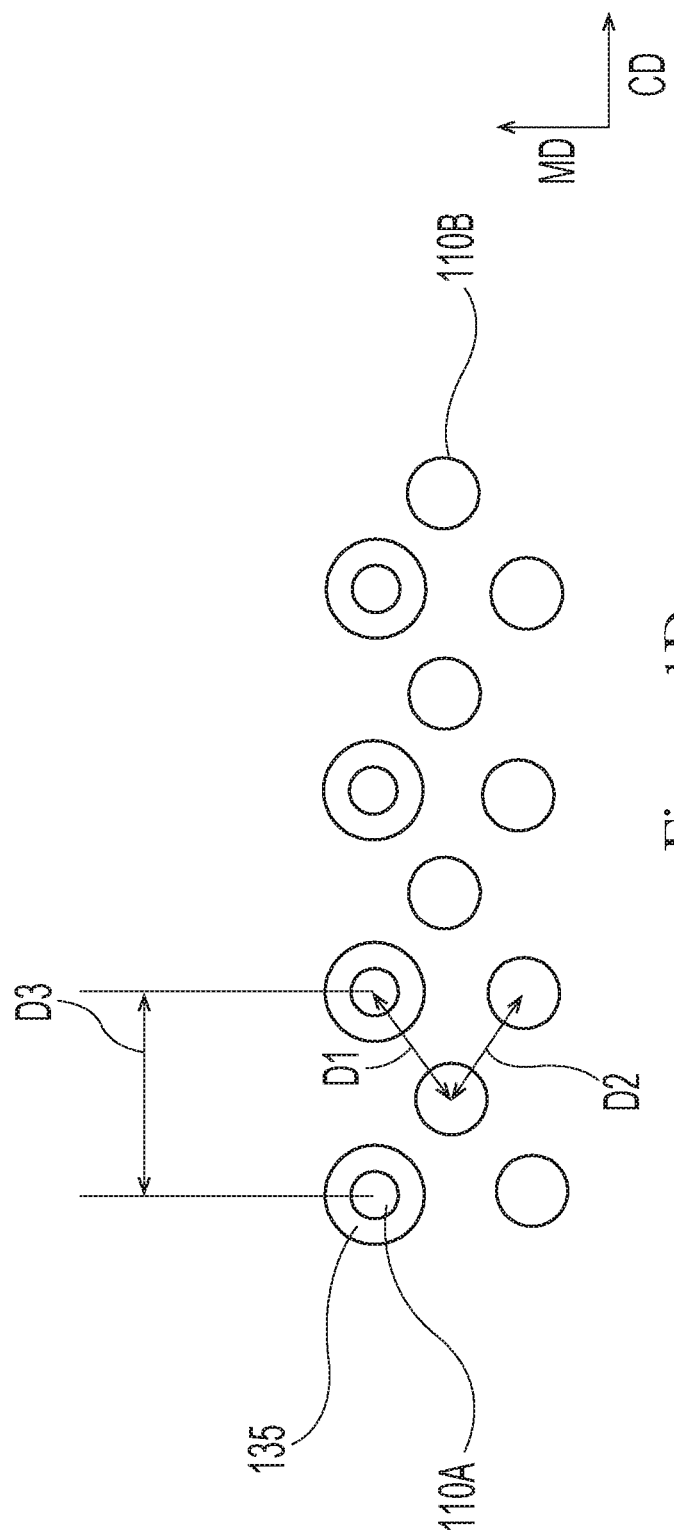
FIG. 1D is plan view showing a plurality of treated apertures and a plurality of untreated apertures.

Referring to FIG. 1D, the number of apertures (treated or untreated) within a zone may comprise any reasonable spacing between the geometric centers of the apertures. The determination of the number of treated apertures within a zone is determined as described herein in the Adjacent Treated Aperture Determination method.

Figure 2A:
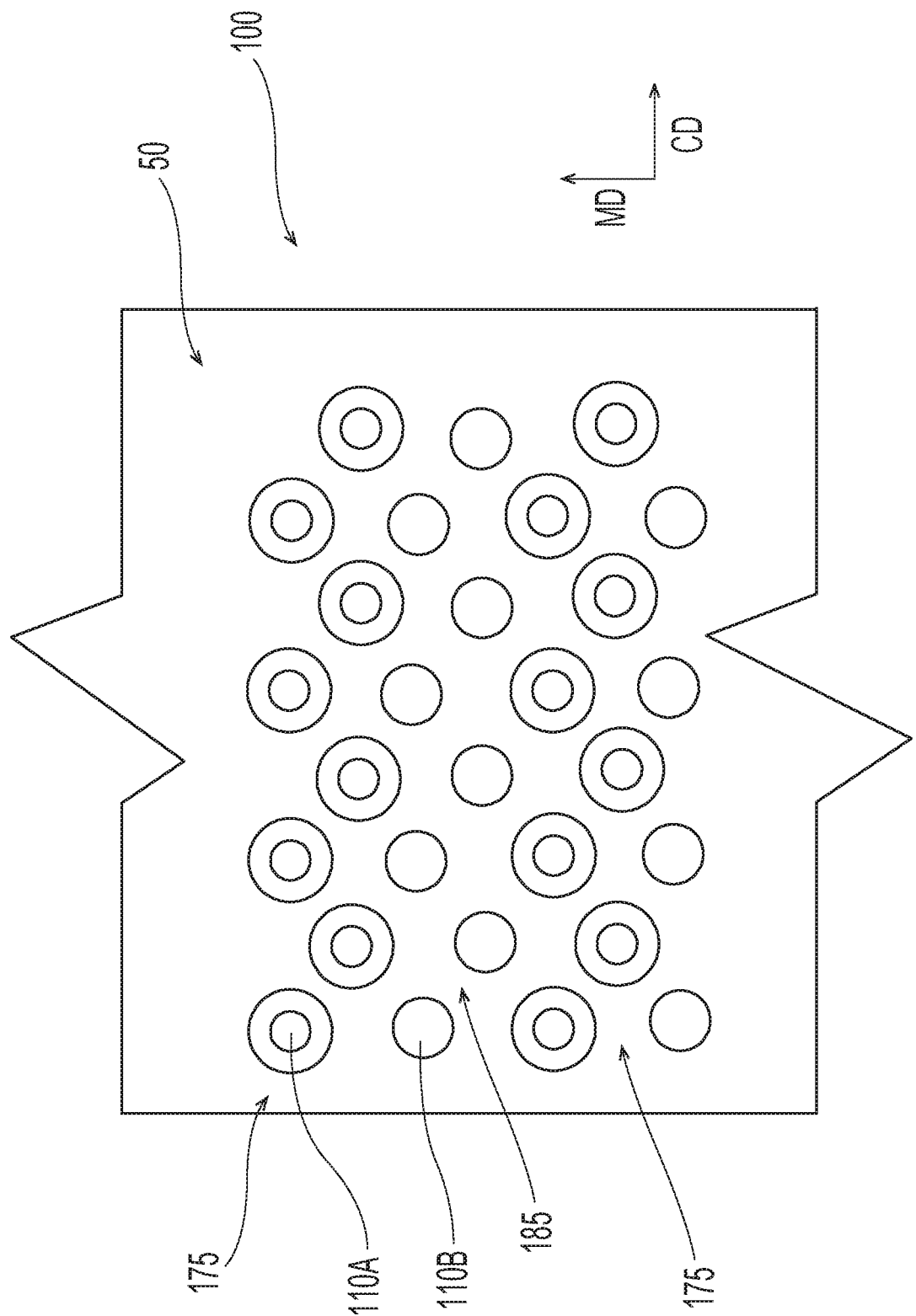
FIG. 2A is a plan view showing the web of FIG. 1A with a different configuration of treated/untreated apertures in accordance with the present disclosure.
Figure 2B:
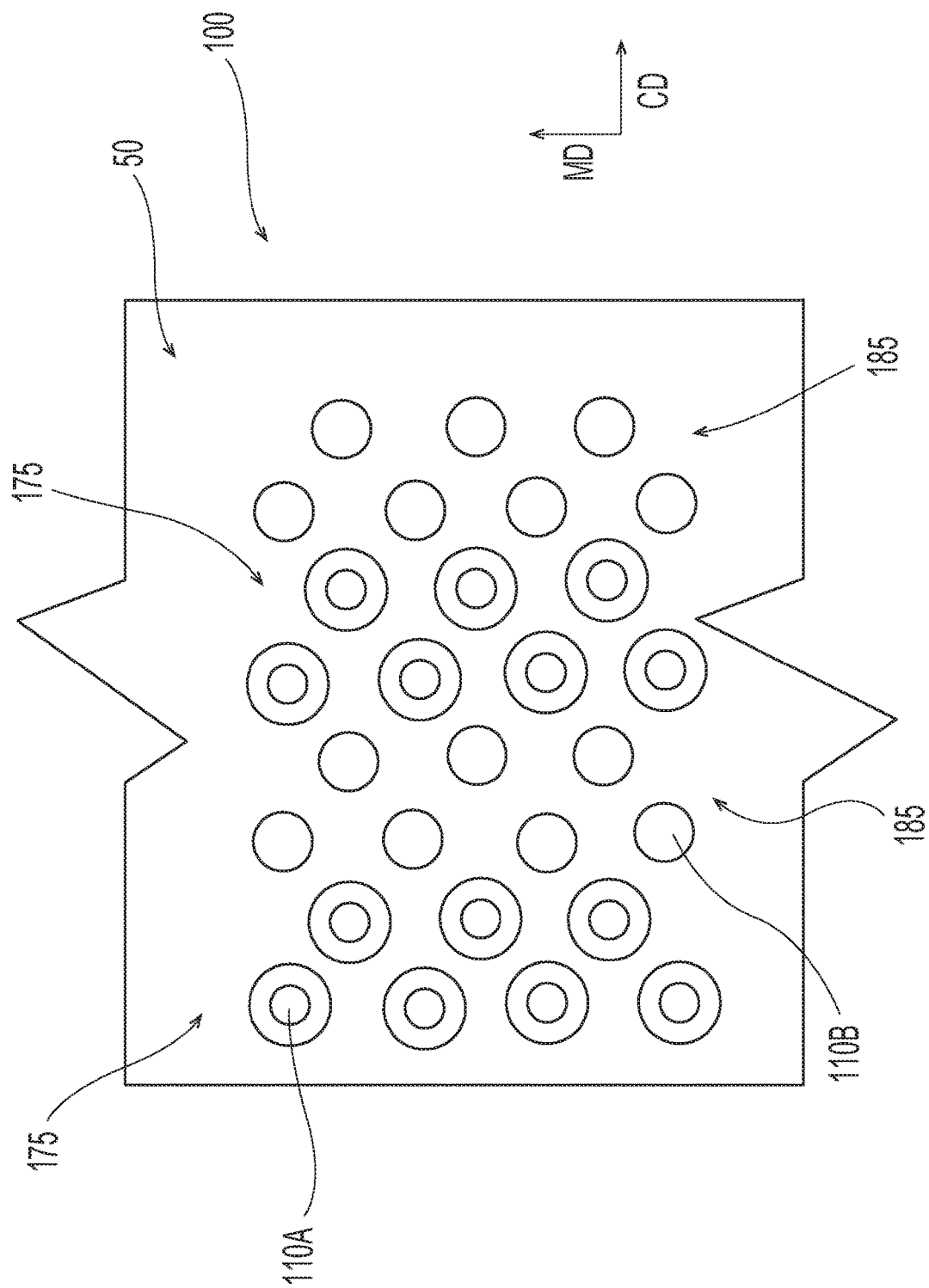
FIG. 2B is a plan view showing the web of FIG. 1A with a different configuration of treated/untreated apertures in accordance with the present disclosure.
Figure 2C:
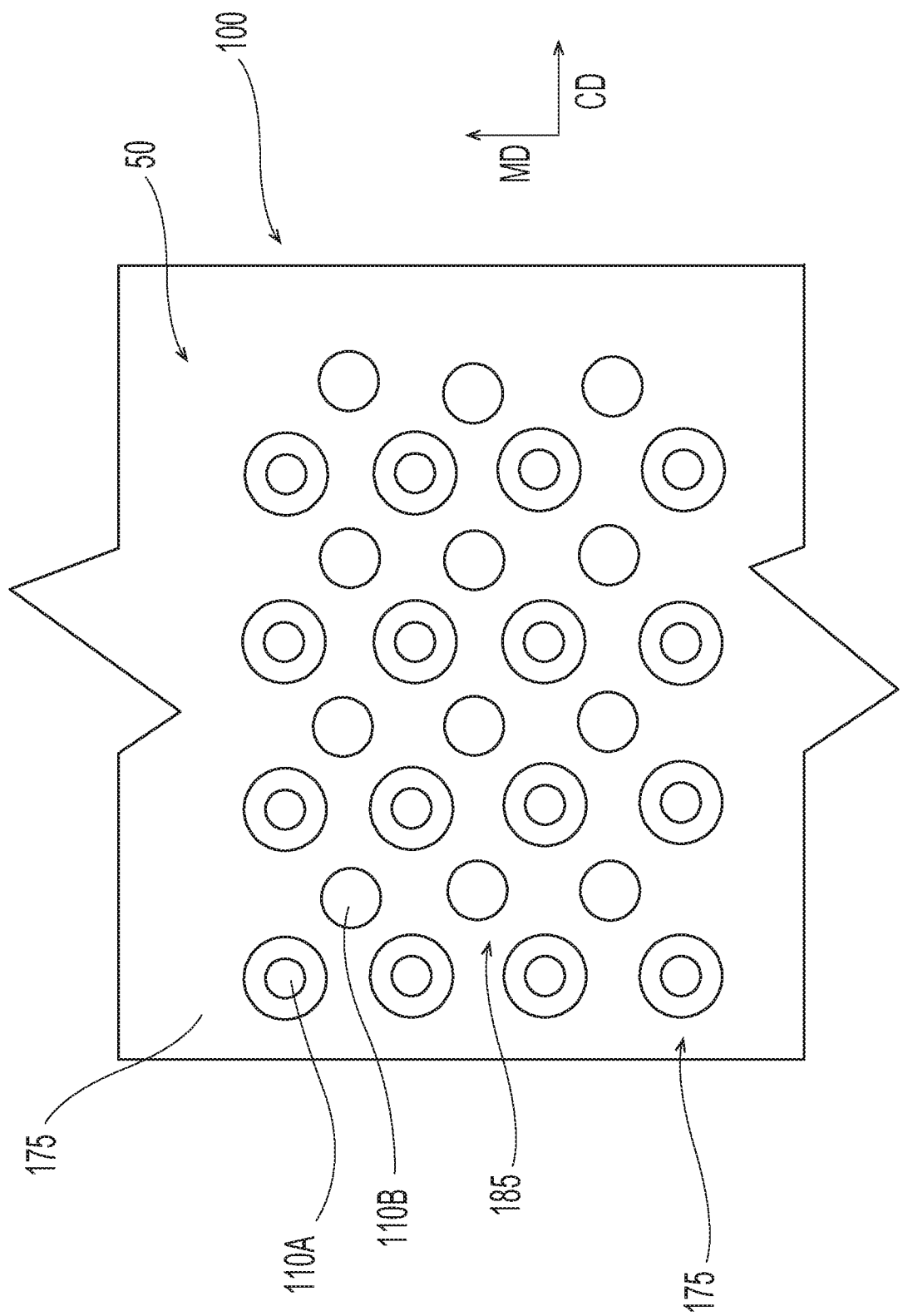
FIG. 2C is a plan view showing the web of FIG. 1A with a different configuration of treated/untreated apertures in accordance with the present disclosure.

As shown in FIG. 2A, in some forms, the treated aperture zones 175 may generally run parallel to the CD. As shown in FIG. 2B, in some forms, the treated aperture zones 175 may generally run parallel to the MD. As shown in FIG. 2C, in some forms, both the treated aperture zones 175 and the untreated apertures zones 185 may comprise one treated aperture 110A and one untreated aperture 110B, respectively.

Figure 3A:
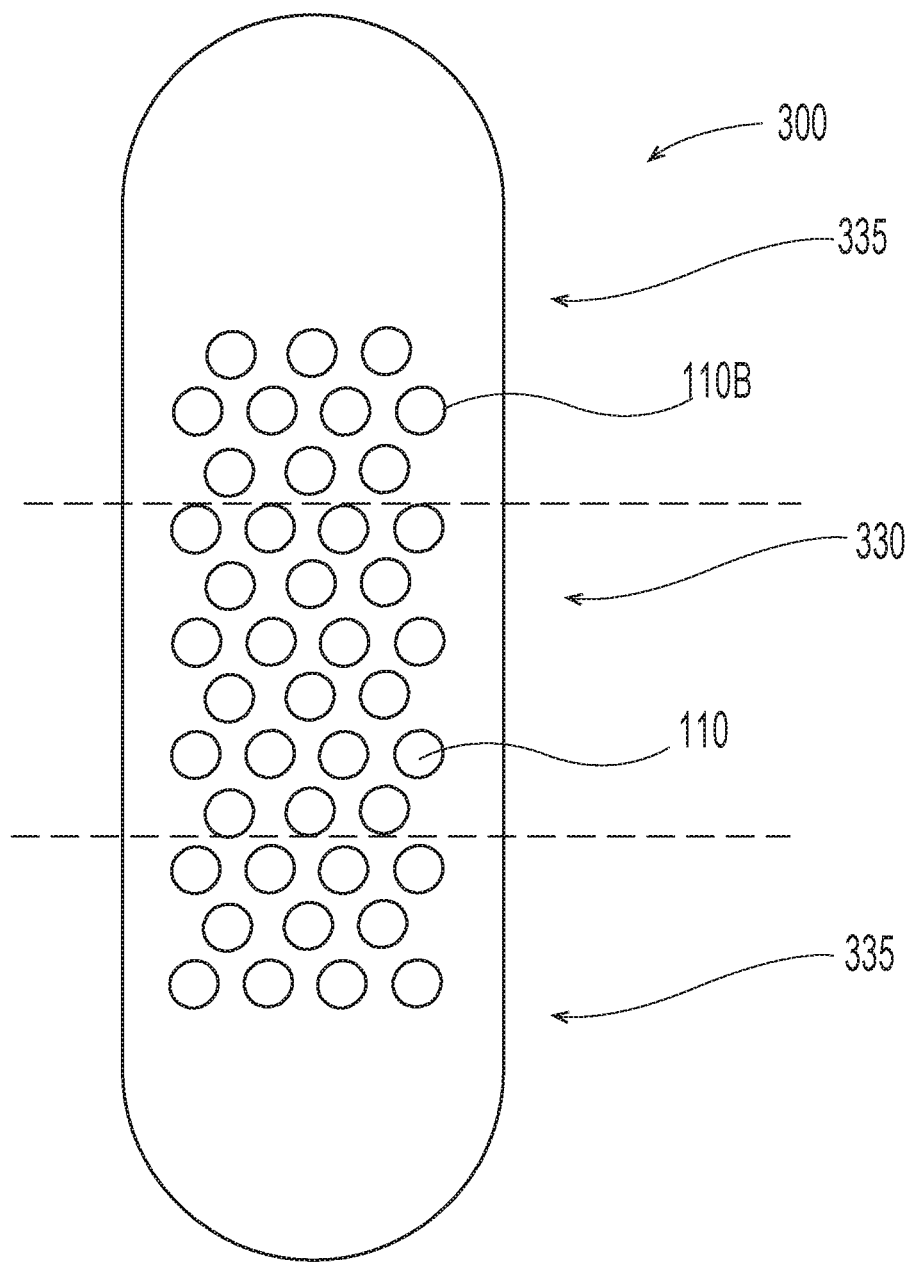
FIGS. 3A-3D are schematic representations of a feminine pad in plan view showing apertures which are exaggerated in size for ease of visualization.
Figure 3B:
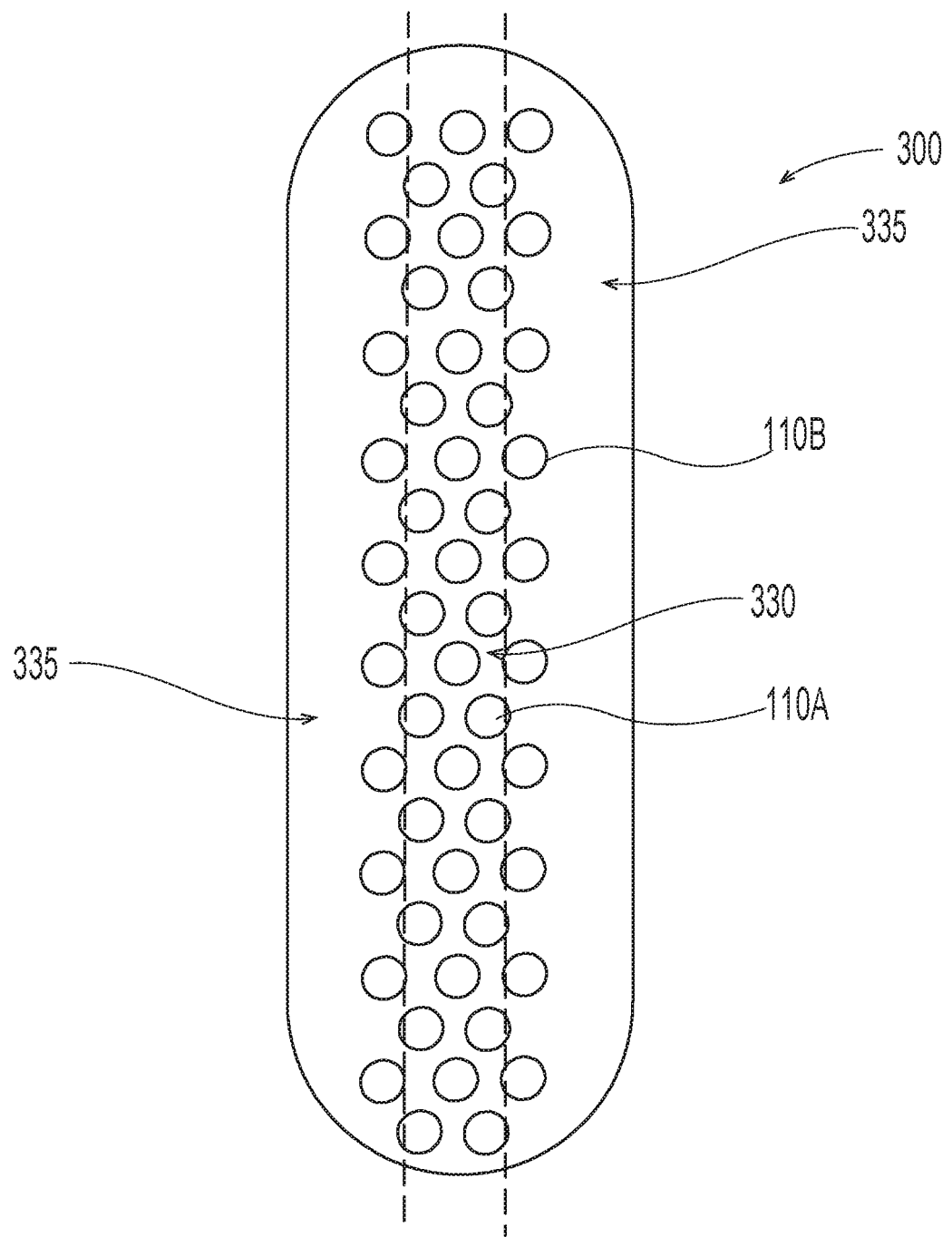
Figure 3C:
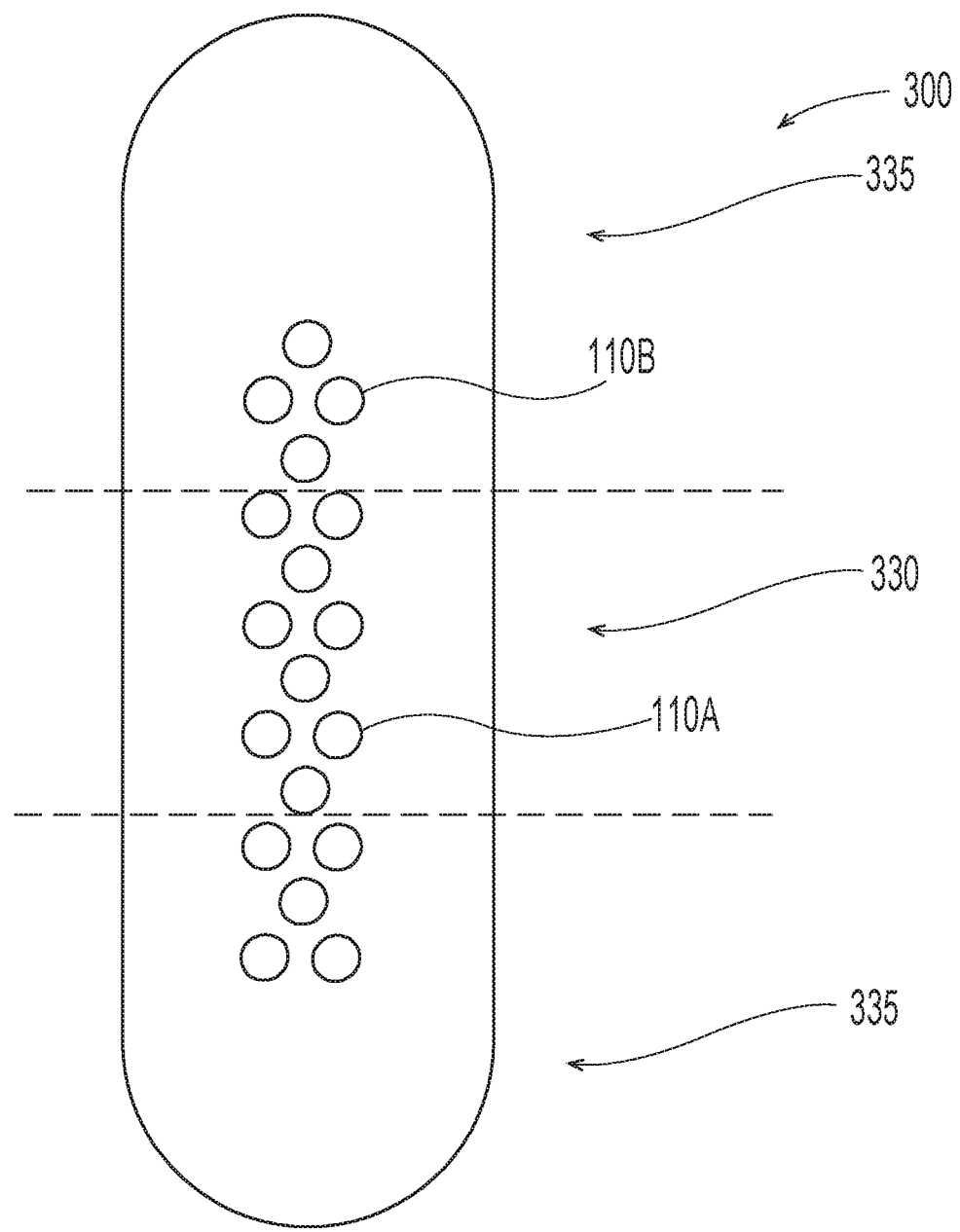

In some forms it may be beneficial to provide treated apertures in zones. For example, a feminine pad 300 may comprise treated apertures provided in a first zone 330 while untreated apertures or a smaller number of apertures (whether treated and/or untreated) are provided in outer zones 335. Some exemplary first zones 330 and outer zones 335 are shown in FIGS. 3A-3B. The first zone 330 along with the outer zones 335 may extend the full length of the feminine pad. For such arrangements, the first zone may comprise between about 20 percent to about 60 percent of the width of the feminine pad. The outer zones 335 may each comprise between about 14 percent to about 40 percent of the width of the feminine pad 300. And where the feminine pad 300 comprises wings, the wings may be comprised by outer zones 335.

An alternate arrangement may comprise the first zone 330 which does not extend the full length of the feminine pad 300. In such arrangements, the first zone 330 may extend the full width of the feminine pad 300 and the outer zones 335 may comprise the ends of the feminine pad 300 and may be disposed on either side of the first zone 330.

Regardless of the arrangement of the first zone 330, the first zone 330 may comprise a target zone. The target zone generally corresponds to the region of intended fluid entry for the feminine pad 300. For menstrual pads, the intended region of fluid entry may be the location on the menstrual pad that corresponds to the vaginal opening. For adult incontinence articles, the intended region of fluid entry may be the location of the incontinence article that corresponds to the urethra or the vulva region as labial tissue can obscure the pathway from the urethra to the absorbent article. And, in general, the target zone may correspond to a portion of the feminine pad 300 that is positioned between the thighs of the wearer during use. The target zone may comprise a transverse centerline and/or the longitudinal centerline of the feminine pad 300. For example, the target zone may be asymmetrically disposed about the transverse centerline, e.g. disposed on one side of the transverse centerline or disposed more on one side of the transverse centerline than the other side of the transverse centerline. A method for determining the extent of the target zone is disclosed hereafter.

The target zone and the first zone 330 may be conterminous. For example, where the first zone does not extend the full length of the feminine pad 300, the first zone and the target zone may have any suitable length. The first zone and/or target zone may extend a distance greater than or equal to about 15 percent of the total length of the article, greater than or equal to about 20 percent of the total length of the article, greater than or equal to about 30 percent of the total length of the article, greater than or equal to about 40 percent of the total length of the article, or greater than or equal to about 50 percent of the total length of the article greater than or equal to about 60 percent of the length of the article, greater than or equal to about 70 percent of the total length of the article, or greater than or equal to about 80 percent of the total length of the article, specifically including all values within these ranges and any ranges created thereby. The width of the target zone may be 100 percent of the width of the article, less than 90 percent, less than 80 percent, less than 70 percent, less than 60 percent, less than 50 percent, less than 40 percent, less than 30 percent, or less than 20 percent, specifically including all values within these ranges and any ranges created thereby.

As shown, the first zone and/or target zone 330 may comprise treated apertures 110A while outside of the target zone 330, i.e. outer zones 335, may comprise untreated apertures 110B. For example, less than about 75 percent of the apertures in the first zone 330 and/or target zone may be treated. In some forms, less than about 60 percent of the apertures in the first zone 330 and/or target zone may be treated. In some forms, less than about 50 percent of the apertures in the first zone and/or target zone may be treated. In some forms, less than about 40 percent of the apertures in the first zone 330 and/or target zone may be treated. In some forms, less than about 30 percent of the apertures in the first zone 330 and/or target zone may be treated. In some forms, less than about 25 percent of the apertures in the first zone 330 and/or target zone may be treated. In some forms, the percentage of treated apertures within the first zone 330 and/or target zone may be between about 12 percent to about 75 percent, from about 20 percent to about 60 percent, or from about 25 percent to about 50 percent, specifically including all numbers within these ranges and any ranges created thereby.

In contrast, the target zone may only comprise a portion of the first zone 330. For example, where the first zone 330 comprises between about 20 percent to about 60 percent of the width of the feminine pad and extends the full length thereof, the target zone may only comprise a portion of the length and/or width of the first zone 330. Specifically, the target zone may comprise between 15 percent and 80 percent of the length of the first zone 330, between 30 percent and 75 percent, or between 40 percent and 60 percent of the length of the first zone 330, specifically reciting all values within these ranges and any ranges created thereby. Additionally, the target zone may also comprise less than 100 percent of the width of the first zone 330 as well. For example, the target zone may comprise between 50 percent and 100 percent of the width of the first zone 330, between 60 percent and 90 percent, or between 70 percent and 85 percent of the width of the first zone 330, specifically reciting all values within these ranges and any ranges created thereby.

As another example, where the first zone 330 extends the full width of the absorbent article but not the full length, the target zone may comprise between 15 percent and 80 percent of the length of the first zone 330, between 30 percent and 75 percent, or between 40 percent and 60 percent of the length of the first zone 330, specifically reciting all values within these ranges and any ranges created thereby. Additionally, the target zone may comprise less than 100 percent of length of the first zone 330. For example, the target zone may comprise between 50 percent and 100 percent of the length of the first zone 330, between 60 percent and 90 percent, or between 70 percent and 85 percent of the length of the first zone 330, specifically reciting all values within these ranges and any ranges created thereby.

As another example in conjunction with or independently of the apertures in the first zone 330 and/or target zone, less than 25 percent of the apertures in the outer zones 335 may be treated. Or, less than about 20 percent of the apertures in the outer zones 335 may be treated, specifically including all numbers within these ranges and any ranges created thereby. As another example, the percentage of treated apertures in the outer zones 335 may be from about 1 percent to about 20 percent or from about 5 percent to about 15 percent or from about 7 percent to about 12 percent or from about 1 percent to about 10 percent or from about 1 percent to about 5 percent, specifically including all numbers within these ranges and any ranges created thereby.

Figure 3D:
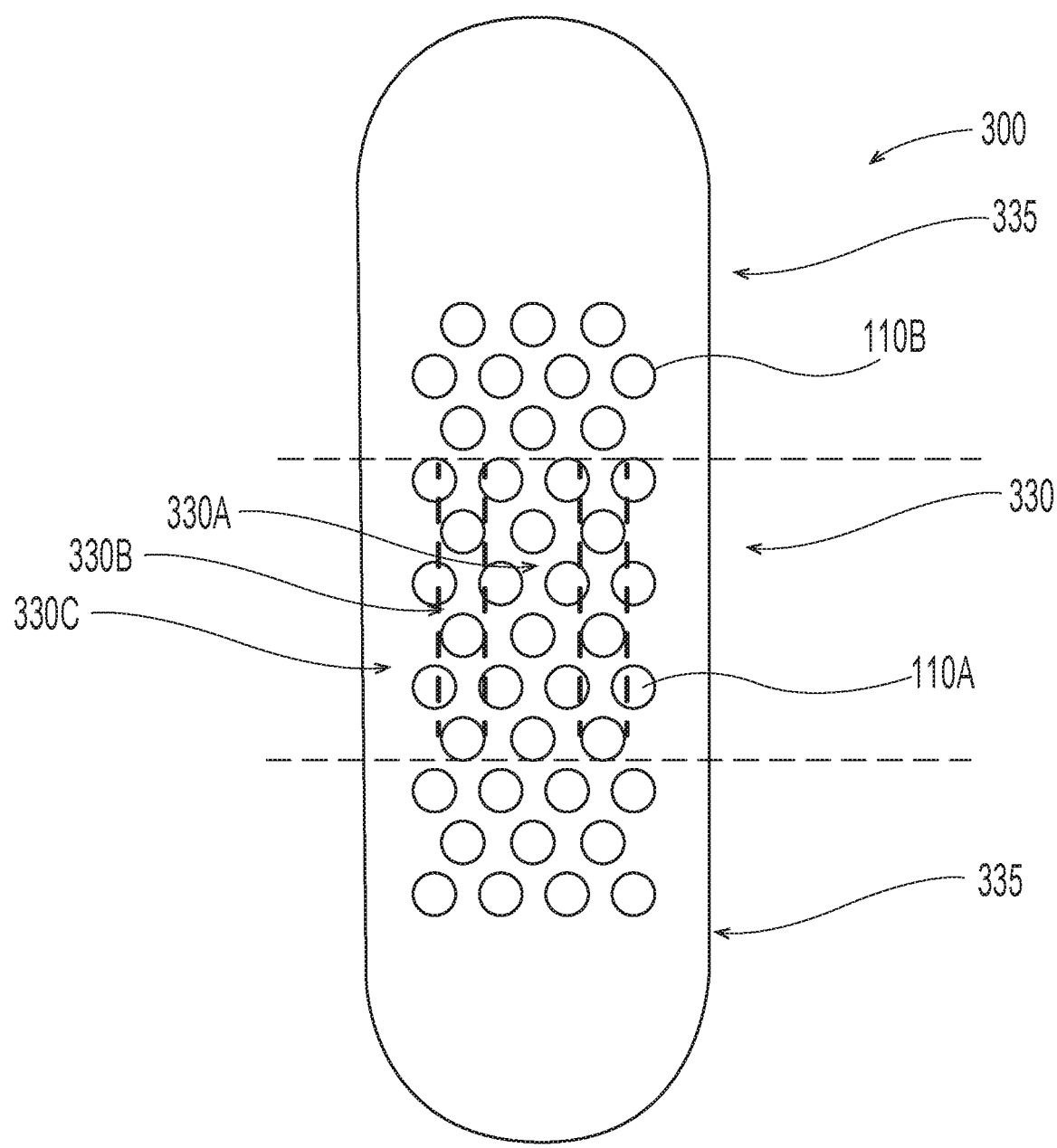

As shown in FIG. 3D, forms of the present disclosure are contemplated where the feminine pad 300 may contain a gradient in the first zone 330. For example, a primary target zone 330A may comprise from between about 75 percent to about 100 percent treated apertures; a secondary target zone 330B, may comprise from about 25 percent to about 75 percent treated apertures, a tertiary target zone 330C may comprise from about 12.5 percent to about 25 percent treated apertures, and the outer zones 335 may comprise from about 0 percent to about 5 percent treated apertures. Forms are contemplated where absorbent articles, e.g. feminine pads, comprise the primary target zone 330A and the secondary target zone 330B but lack the tertiary target zone. Additional forms are contemplated where absorbent articles, e.g. feminine pads, comprise the primary target zone 330A and the tertiary target zone 330C but lack the secondary target zone 330B. Additionally, the gradient ay extend to the outer zones 335 such that the primary target zone 330A, the secondary target zone 330B, and/or the tertiary target zone 330C extend into the outer zones 335. For example, the primary target zone 330A, the secondary target zone 330B, and/or the tertiary target zone 330C may extend the full length of the feminine pad 300.

The inventors have surprisingly found that good acquisition and good rewet properties can be achieved by appropriately configuring treated aperture zones and untreated aperture zones. The results are provided in Tables 1-3. Regardless of the configuration of the target zone as described herein, it is believed that the configuration of treated apertures and untreated apertures within a target zone and/or outer zone can provide similar results.

Samples:

Each of the samples numbered 1 through 7, data for which is provided in Table 1, was constructed as follows.

Each of the samples comprised a 75 gsm spunlace secondary topsheet and a 200 gsm Alco G2 absorbent core. The secondary topsheet and the absorbent core are currently available in Always Ultra Thin products. The topsheet, secondary topsheet, and absorbent core were attached to one another via hot melt adhesive H2031, available from Henkel, at a basis weight of 0.005 g/square inch.

Each of the samples comprised a dual layer topsheet. Each dual layer topsheet comprised a hydrophobic layer and a hydrophilic layer. The hydrophobic layer was a 25 gsm, spunbond nonwoven with 2.5 denier per filament, 30/70 polyethylene/polypropylene sheath/core bi-component filaments from Fibertex Personal Care in Nilai, Malaysia. The filaments of the hydrophobic layer comprised 17 percent of glycerol tristearate masterbatch in the sheath component only.

The hydrophilic layer was a 28 gsm, spunbond nonwoven with 2.8 denier per filament, 50/50 sheath/core polyethylene/polypropylene bi-component filaments, from Fitesa in Washougal, Wash. The hydrophilic layer was coated with 0.4 percent by weight Silastol PHP26 surfactant made by Schill & Seilacher, Germany.

Each of the topsheets for the samples comprised apertures. The apertures were arranged in columns and rows. Adjacent columns of apertures had offset rows of apertures. So for example, in the MD direction, Column A of apertures may have apertures in rows 1, 3, 5, and so on. Column C may similarly be configured. However, Column B—disposed between Columns A and C—may have apertures in rows 2, 4, 6, 8, and so on. Column D was configured similarly to Column B. Each of the topsheets was apertured in accordance with the process described in U.S. Pat. Nos. 5,658,639; 5,628,097; 5,916,661; 7,917,985; and U.S. Patent Application Publication No. 2003/0021951.

In such processing, the hydrophobic and hydrophilic layers were laminated in a first process that created a plurality of melt stabilized areas in the laminate. In a second process, the laminate was then stretched to such an extent that the melt stabilized areas broke and formed apertures. The melt stabilized areas can be approximated by a rectangular shape having a length of 2.54 mm and a width of 0.25 mm.

Some of the samples below comprised treated apertures. In such samples, a composition was applied to a percentage of the melt stabilized areas. The composition was applied at a basis weight of 1 gsm of surfactant over the melt stabilized area via ink jet printing. The process of ink jet printing onto melt stabilized areas and/or onto apertures was disclosed in U.S. Patent Application Publication No. 2017/0225449, and is discussed in additional detail herein. The composition was 75 percent by weight of Stantex S6327 from Pulcra Chemicals and 25 percent by weight ethanol.

Sample 1: none of the apertures (melt stabilized areas) were treated with the composition;

Sample 2: 12.5 percent of the apertures (melt stabilized areas) were treated with the composition.

Sample 3A: 25 percent of the apertures (melt stabilized areas) were treated with the composition. The 25 percent were clustered such that the majority of treated aperture zones comprised more than one treated aperture.

Sample 3B: 25 percent of the apertures (melt stabilized areas) were treated with the composition. The 25 percent were distributed such that the majority of treated aperture zones comprised only one treated aperture per zone.

Sample 4A: 50 percent of the apertures (melt stabilized areas) were treated with the composition. The 50 percent were clustered such that the majority of treated aperture zones comprised more than one treated aperture.

Sample 4B: 50 percent of the apertures (melt stabilized areas) were treated with the composition. The 50 percent were distributed such that the majority of treated aperture zones comprised only one treated aperture per zone.

Sample 5A: 75 percent of the apertures (melt stabilized areas) were treated with the composition. The 75 percent were clustered such that the majority of treated aperture zones comprised more than one treated aperture.

Sample 5B: 75 percent of the apertures (melt stabilized areas) were treated with the composition. The 75 percent were distributed such that the majority of treated aperture zones comprised only one treated aperture per zone.

Sample 6: 100 percent of the apertures (melt stabilized areas) were treated with the composition.

Sample 7: The top layer of the topsheet was rendered hydrophilic by treating a 50 mm by 50 mm area with the composition.

Each of the above samples was tested regarding acquisition speed for multiple liquid insults, rewet, and stain masking. For acquisition speed in seconds, data is provided in Table 1.

TABLE 1

| Sample No. | Acquisition Speed - first insult | Acquisition Speed - second insult | Acquisition Speed - third insult |
| --- | --- | --- | --- |
| 1 | 120 | 120 | 120 |
| 2 | 120 | 120 | 120 |
| 3A | 120 | 120 | 120 |
| 3B | 120 | 84.7 | 84.7 |
| 4A | 120 | 85.3 | 26.0 |
| 4B | 87.3 | 20.3 | 19.0 |
| 5A | 120 | 15.3 | 18.7 |
| 5B | 89.3 | 16.7 | 18.3 |
| 6 | 84.7 | 13.7 | 17.3 |
| 7 | 3.0 | 3.7 | 5.3 |

Data for the samples regarding rewet is provided in Table 2.

TABLE 2

| Sample No. | Rewet |
| --- | --- |
| 1 | 0.266667 |
| 2 | 0.2113 |
| 3A | 0.249433 |
| 3B | 0.2325 |
| 4A | 0.176267 |
| 4B | 0.248733 |
| 5A | 0.3185 |
| 5B | 0.356867 |
| 6 | 0.3272 |
| 7 | 0.538733 |

Data for the above samples regarding stain intensity is provided below with regard to Table 3.

TABLE 3

| Sample No. | Stain Intensity |
| --- | --- |
| 1 | 51.5 |
| 2 | 46.0 |
| 3A | 39.4 |
| 3B | 42.5 |
| 4A | 34.7 |
| 4B | 35.0 |
| 5A | 38.7 |
| 5B | 38.9 |
| 6 | 39.4 |
| 7 | 85.1 |

As shown in Tables 1 through 3, the number of treated apertures can impact the acquisition, rewet and stain intensity. Additionally, whether the treated aperture zone comprises more than one treated aperture can similarly impact the acquisition, rewet, and stain intensity. For example, treated aperture zones which are clustered, i.e. more than on treated aperture per zone for the majority of zones, can provide better rewet properties, but may negatively impact acquisition speed. For the sake of the present disclosure, the inventors have found that treated aperture zones may comprise one or more apertures and wherein the treated aperture zones comprise between 18 percent and 70 percent, between 20 percent and about 65 percent, or between 25 percent and about 50 percent of the plurality of apertures of the absorbent article, specifically reciting all values within these ranges and any ranges created thereby.

Additionally, as shown in the Tables, the treated aperture density can impact acquisition and rewet. For example, the inventors contemplate treated aperture zones wherein none of the plurality of treated aperture zones comprises more than about 75 percent of the plurality of treated apertures, no more than about 50 percent of the plurality of treated apertures, no more than about 40 percent of the plurality of treated apertures, no more than about 30 percent of the plurality of treated apertures, no more than about 20 percent of the plurality of treated apertures, or no more than about 10 percent of the plurality of treated apertures, specifically reciting all values within these ranges and any ranges created thereby.

Precursor Web

As discussed previously, the precursor web may comprise a single layer or multiple layers of material. For example, the precursor web may comprise a nonwoven layer. As another example, the precursor web may comprise a film layer. Still in other examples, the precursor web may comprise a laminate which includes multiple nonwoven layers, multiple film layers, or a combination thereof.

The precursor web may comprise any suitable material. Some suitable examples include nonwovens, wovens, cellulosic materials, films, elastic materials, non-elastic materials, high-loft materials, and/or foams. The precursor webs may also comprise one or more layers of one or more nonwoven materials, one or more films, combinations of different nonwoven materials, combinations of different films, combinations of one or more films and one or more nonwoven materials, or combinations of one or more different materials, for example. Precursor webs having one or more layers of the same or similar materials are also within the scope of the present disclosure.

As another example, the precursor web may comprise a layer comprising a plurality of substrates. For example, the precursor web may comprise a spunbonded nonwoven as a layer. The spunbonded nonwoven may comprise a plurality of substrates which can be integrally formed with one another. For example, substrates may be produced via a spunbond process. A first substrate may be produced by a first spin beam and a second substrate may be produced via a second spin beam. Additional substrates may be produced via additional spin beams on the same spunbond manufacturing line.

Precursor webs may comprise any suitable material. For example, precursor web materials may comprise PE/PP bi-component fiber spunbond webs. Other suitable precursor webs may comprise spunbond webs comprising side-by-side crimped fibers (e.g. PE/PP or PP/PP) that are bonded via calendar (thermal point) bonding or through-air bonding. For those configurations with multiple layers a first layer and second layer of the patterned apertured web of the present invention may comprise a crimped spunbond layer. For these configurations, the crimped spunbond layers may be combined from roll stock and joined as provided herein. However, where the precursor web comprises a first substrate and a second substrate, each may be crimped spunbond substrates formed on a spunbond manufacturing line where the first substrate is formed from a first spin beam while the second substrate is formed from a second spin beam.

Other suitable precursor webs may comprise carded staple fibers comprising polypropylene, polyethylene terephthalate, polyethylene/polypropylene bi-component, polyethylene/polyethylene terephthalate bi-component, or the like, which are calendar bonded, through-air bonded, resin bonded or hydroentangled. The precursor webs may comprise microfibers and/or nanofibers, optionally with other fibers. In some circumstances, multiple layer webs may be desired over a single layer webs (even at the same basis weight) due to increased uniformity/opacity and the ability to combine webs having different properties. For example, an extensible spunbond nonwoven carrier layer may be combined with a soft, crimped fiber nonwoven (spunbond or carded). The substrates may have the same or different surface energy, for example, the top layer may be hydrophobic and the lower layer may be hydrophilic. The layers may have different permeability/capillarity, e.g. the upper layer may have higher permeability and the lower layer have higher capillarity in order to set up a capillary gradient and aid in moving fluid away from the surface (or topsheet) of an absorbent article and into an absorbent core of the absorbent article.

Additionally, the precursor webs may comprise a surface treatment and/or additive to the constituent material of the precursor web. For example, the precursor web may comprise a hydrophobic surface treatment. For such webs, a composition applied in a composition site may be hydrophilic. Still in other examples, the precursor web may comprise a hydrophilic surface treatment or the constituent material of the precursor web may comprise hydrophilic material. For such webs, a composition applied in a composition site may be hydrophobic. As another example, precursor webs of the present invention may comprise a melt additive. In one specific example, the precursor web may comprise fibers which comprise a hydrophobic melt additive. In such example, at least one of the composition sites may comprise a hydrophilic composition. One particularly suitable melt additive comprises glycerol tristearate.

The inventors have surprisingly found that the addition of some surfactants to a phobically treated web—via surface treatment and/or melt additive—can reduce the migration of the surfactant. Additional detail regarding this discovery, among other features, is provided in U.S. Application Ser. No. 62/689,909, entitled ABSORBENT ARTICLE WITH TOPSHEET TREATED TO REDUCE SURFACTANT MIGRATION.

Additional suitable melt additives and surface treatments of materials is discussed in additional detail in U.S. Pat. Nos. 8,178,748, 8,026,188; 4,578,414; 5,969,026; U.S Patent Application Publication Nos. 2012/0100772; 2014/0272261; 2012/0296036; 2014/0087941; 2016/0067118; 2014/0272359; European Patent No. 2411061; and PCT Patent Application Publication No. 2012/162130.

Other suitable materials for precursor webs include films. Some suitable films are described in U.S. Pat. Nos. 3,929,135; 4,324,426; 4,324,314; 4,629,643; 4,463,045; and 5,006,394.

Compositions

As mentioned previously, webs of the present invention may comprise apertures with compositions, i.e. treated apertures. In some forms, the composition may be hydrophilic. Some suitable examples of hydrophilic compositions include a surfactant or combination of surfactants with hydrophilic/lyophilic balance number (HLB) of greater than or equal to about 7, more desirably greater than or equal to about 10, and even more desirably, a HLB of greater than or equal to about 14. Hydrophilic agents that do not generally have a measured HLB may also be used.

Additional examples of hydrophilic compositions include non-ionic surfactants including esters, amides, carboxylic acids, alcohols, ethers—polyoxyethylene, polyoxypropylene, sorbitan, ethoxylated fatty alcohols, alyl phenol polyethoxylates, lecithin, glycerol esters and their ethoxylates, and sugar based surfactants (polysorbates, polyglycosides). Other suitable nonionic surfactants include: ethoxylates, including fatty acid ester ethoxylates, fatty acid ether ethoxylates, and ethoxylated sugar derivatives (e.g., ethoxylated fatty acid polyesters, ethoxylated fatty acid sorbitan esters, and the like), and the like, as well as combinations comprising at least one of the foregoing. Other suitable examples include anionic surfactants including sulfonates, sulfates, phosphates, alkali metal salts of fatty acids, fatty alcohol monoesters of sulfuric acid, linear alkyl benzene sulfonates, alkyl diphenyloxide sulfonates, lignin sulfonates, olefin sulfonates, sulfosuccinates, and sulfated ethoxylates of fatty alcohols. Other suitable examples include cationic surfactants including amines (primary, secondary, tertiary), quaternary ammoniums, pyridinium, quaternary ammonium salts—QUATS, alkylated pyridinium salts, alkyl primary, secondary, tertiary amines, and alkanolamides. Other suitable examples include zwiterionic surfactants including amino acids and derivatives, amine oxide, betaines, and alkyl amine oxides. Other suitable examples include polymeric surfactants including polyamines, carboxylic acid polymers and copolymers, EO/PO block copolymers, ethylene oxide polymers and copolymers, and polyvinylpyrrolidone. Other suitable examples include silicone surfactants including dimethyl siloxane polymers with hydrophile. And other suitable examples include perfluorocarboxylic acid salts and fluorosurfactants.

The hydrophilic agents that do not generally have a measured HLB may also be used. Such hydrophilic agents may include, without limitation, diols, such as glycols and polyglycols. Suitable nonionic surfactants include, but are not intended to be limited to, C2-8 diols and polyglycols, and the like. Generally, the diol may be glycols (C2 and C3 diols) and polyglycols. The term "polyglycol" refers to a dihydroxy ether formed by dehydration of two or more glycol molecules. A representative, non-limiting list of useful polyglycols, includes: ethylene glycol, propylene glycol, polyethylene glycols, polypropylene glycols, methoxypolyethylene glycols, polybutylene glycols, block copolymers of butylene oxide and ethylene oxide, and the like, as well as combinations comprising at least one of the foregoing.

Additionally, suitable philic composition include finishing treatments which are typically proprietary blends of synthetic surfactant solutions which are commercially available. Examples include materials from Schill & Seilacher AG under the tradename Silastol (e.g. Silastol PHP 26, Silastol PHP 90, Silastol PST-N, Silastol PHP 207, Silastol PHP 28 & Silastol PHP 8), from Pulcra Chemicals under the tradename Stantex® (e.g. Stantex S 6327, Stantex S 6087-4, & Stantex PP 602), among others.

Forms are contemplated where at least a portion of the web 100 (see FIG. 1A) is treated in the land areas 51 (see FIG. 1A) with a hydrophobic composition and/or a blood modifying agent. Some suitable examples of hydrophobic compositions include fluorinated or perfluorinated polymers; silicones; fluorochemicals; zirconium compounds; oils; latexes; waxes; crosslinking resins; and blends thereof; fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets; nanostructured particles selected from fumed silica, hydrophobic titania, zinc oxide, nanoclay, and mixtures thereof; fats and oils, glycerol derivatives; hydrophobic silicones or suitable combinations thereof.

Examples of suitable silicone polymers are selected from the group consisting of silicone MQ resins, polydimethysiloxanes, crosslinked silicones, silicone liquid elastomers, and combinations thereof. Polydimethylsiloxanes can be selected from the group consisting of vinyl-terminated polydimethsiloxanes, methyl hydrogen dimethylsiloxanes, hydroxyl-terminated polydimethysiloxanes, organo-modified polydimethylsiloxanes, and combinations thereof, among others.

Other hydrophobic materials suitable for the present invention are well defined and documented in the art. For example, US Patent Application Publication No. 2002/0064639 describes hydrophobic compositions selected from the group consisting of silicones, fluorochemicals, zirconium compounds, oils, latexes, waxes, crosslinking resins, and blends thereof. Representative water repellent fluorochemical compounds described in U.S. Pat. No. 7,407,899 include fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets. U.S. Pat. No. 6,548,732 describes hydrophobic substances from the group consisting of theobroma oil, cacao butter, cocoa butter, petrolatum, mineral jelly, white mineral oil, dimethicone, zinc oxide preparation, chinese white, zinc white, beeswax, lanolin, jojoba oil and combinations thereof. Additionally, U.S. application Ser. No. 13/193,065, filed Jul. 28, 2011 discusses substrates that exhibit superhydrophobic properties when treated with a composition comprising a hydrophobic component selected from fluorinated polymers, perfluorinated polymers, and mixtures thereof; nano-structured particles selected from fumed silica, hydrophobic titania, zinc oxide, nanoclay, and mixtures thereof; and water for an overall water-based, non-organic solvent. Examples of such compositions and surfaces in U.S. application Ser. No. 13/193,065, filed Jul. 28, 2011 exemplify the superhydrophobic treated surfaces that may be used as the nonwoven topsheet of the present invention.

Additionally, waxes and other hydrophobic materials can be used, including petroleum-based emollients; fatty acid esters; polyol polyesters; fatty alcohol ethers; sterols and sterol esters, and their derivatives; triglycerides; glyceryl esters; ceramides; and mixtures thereof. The fatty acids may originate from vegetable, animal, and/or synthetic sources. Some fatty acids may range from a C8 fatty acid to a C30 fatty acid, or from a C12 fatty acid to a C22 fatty acid. In another embodiment, a substantially saturated fatty acid may be used, particularly when saturation arises as a result of hydrogenation of fatty acid precursor. Examples of fatty acid derivatives include fatty alcohols, fatty acid esters, and fatty acid amides.

Suitable fatty alcohols (R—OH) include those derived from C12-C28 fatty acids.

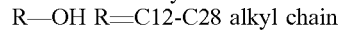
R—OH R=C12-C28 alkyl chain

Suitable fatty acid esters include those fatty acid esters derived from a mixture of C12-C28 fatty acids and short chain (C1-C8, preferably C1-C3) monohydric alcohols preferably from a mixture of C12-C22 saturated fatty acids and short chain (C1-C8, preferably C1-C3) monohydric alcohols. The hydrophobic melt additive may comprise a mixture of mono, di, and/or tri-fatty acid esters. An example includes fatty acid ester with glycerol as the backbone.

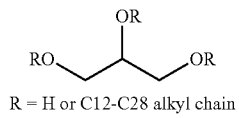
R = H or C12-C28 alkyl chain

The glycerol derived fatty acid ester has at least one alkyl chain, at least two, or three chains to a glycerol, to form a mono, di, or triglyceride. Suitable examples of triglycerides include glycerol thibehenate (C22), glycerol tristearate (C18), glycerol tripalmitate (C16), and glycerol trimyristate (C14), and mixtures thereof. In the case of triglycerides and diglycerides, the alkyl chains could be the same length, or different length. Example includes a triglyceride with one alkyl C18 chain and two C16 alkyl chain, or two C18 alkyl chains and one C16 chain. Preferred triglycerides include alkyl chains derived from C14-C22 fatty acids.

Suitable fatty acid amides include those derives from a mixture of C12-C28 fatty acids (saturated or unsaturated) and primary or secondary amines. A suitable example of a primary fatty acid amide includes those derived from a fatty acid and ammonia.

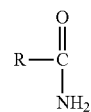
R = C12-C28 alkyl chain

Suitable examples include erucamide, oleamide and behanamide. Other suitable hydrophobic melt additives include hydrophobic silicones, ethoxylated fatty alcohols.

The blood modifying agent of this disclosure can have an IOB of about 0.00-0.60, a melting point of no higher than about 45 deg. C., a water solubility of about 0.00-0.05 g at 25 deg. C., and a weight-average molecular weight of less than about 1,000. The IOB (Inorganic Organic Balance) is an indicator of the hydrophilic-lipophilic balance, and as used herein, it is the value calculated by the following formula by Oda et al. inorganic value/organic value. The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725 which is incorporated by reference herein.

Preferably, the blood modifying agents is selected from the group consisting of following items (i)-(iii), and any combination thereof: (i) a hydrocarbon; (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety. As used herein, "hydrocarbon" refers to a compound composed of carbon and hydrogen, and it may be a chain hydrocarbon, such as, a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as, aromatic hydrocarbons and alicyclic hydrocarbons.

Examples of suitable blood modifying agents include esters of chain hydrocarbon polyols. The polyol may have 2-5 alcohol groups on a 2-5 carbon backbone, and between 1 and 5 of the alcohols may be derivatives with a fatty acid having between 4-22 carbon atoms and 0 to 4 double bonds. Suitable examples include triesters of glycerin and fatty acids, represented by formula (5):

(5)

diesters of glycerin and fatty acids, represented by the following formula (6):

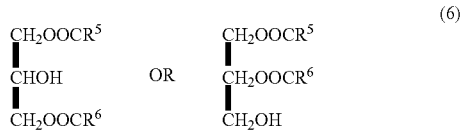

(6)

and monoesters of glycerin and fatty acids, represented by the following formula (7):

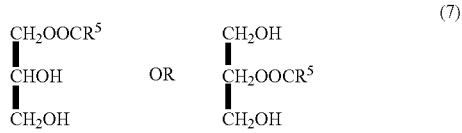

(7)

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the JOB, melting point and water solubility. The esters of glycerin and a fatty acid is preferably a diester or triester, and more preferably a triester. A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing. Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_H$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

Additionally, in some forms, in conjunction with the hydrophilic compositions and/or blood modifying compositions described herein, or independent therefrom, compositions applied to at least a portion of the land areas 51 (See FIG. 1A) may comprise a lotion. Such deposition is believed to reduce the likelihood of rewet. Additionally, the lotions may provide skin benefits as described herein.

Any suitable lotion may be utilized as a composition of the present invention. Some suitable lotions are described in U.S. Patent Application Publication Nos. 2003/0206943 and 2007/0219515. Lotions suitable for use as compositions in the present invention may comprise from about 60-99.9 percent of a carrier. Suitable carrier compounds include petroleum-based hydrocarbons having from about 8 to about 32 carbon atoms, fatty alcohols having from about 12 to about 18 carbon atoms, polysiloxane compounds, fatty acid esters, alkyl ethoxylates, lower alcohols having from about 2 to about 6 carbon atoms, low molecular weight glycols and polyols, fatty alcohol ethers having from about 12 to about 22 carbon atoms in their fatty chain, lanolin and its derivatives, ethylene glycol derivatives of $C_{12}$-$C_{22}$ fatty acids, glyceride and its derivatives including acetoglycerides and ethoxylated glycerides of $C_{12}$-$C_{18}$ fatty acids, and mixtures thereof. Other suitable carriers include oils or fats, such as natural oils or fats, or natural oil or fat derivatives, in particular of plant or animal origin. Suitable carriers further encompass waxes. As used herein, the term 'wax' refers to oil soluble materials that have a waxy constituency and have a melting point or range of above ambient temperature, in particular above 25° C. Waxes are materials that have a solid to semi-solid (creamy) consistency, crystalline or not, being of relative low viscosity a little above their liquefying point. Suitable waxes which can be incorporated into the lotion composition include animal, vegetable, mineral or silicone based waxes which may be natural or synthetic, and including mixtures thereof.

Additionally, lotions suitable for use with the present invention may comprise optional ingredients such as skin treatment agents including hexamidine, zinc oxide, and niacinamide, glycerine, chamomile, panthenol, fats and oils, and/or skin conditioning agents, perfumes, deodorants, opacifiers, astringents, preservatives, emulsifying agents, film formers, stabilizers, proteins, lecithin, urea, colloidal oatmeal, pH control agents. Additional optional ingredients include particles, wetting agents, and/or viscosity or thickening agents.

Web Processing

The compositions may be applied to a web in any suitable manner. In some forms, the composition may be applied by hand via a small brush or pipette. In other forms, the composition may be applied to the apertures via printing. Some suitable examples of printing include flexographic, videojet, and inkjet. Exemplary printing processes are provided with regard to FIGS. 4A to 8C. The printing process may be preferable where higher production speeds are required compared to what may be achievable via brush and/or pipette.

Figure 4A:
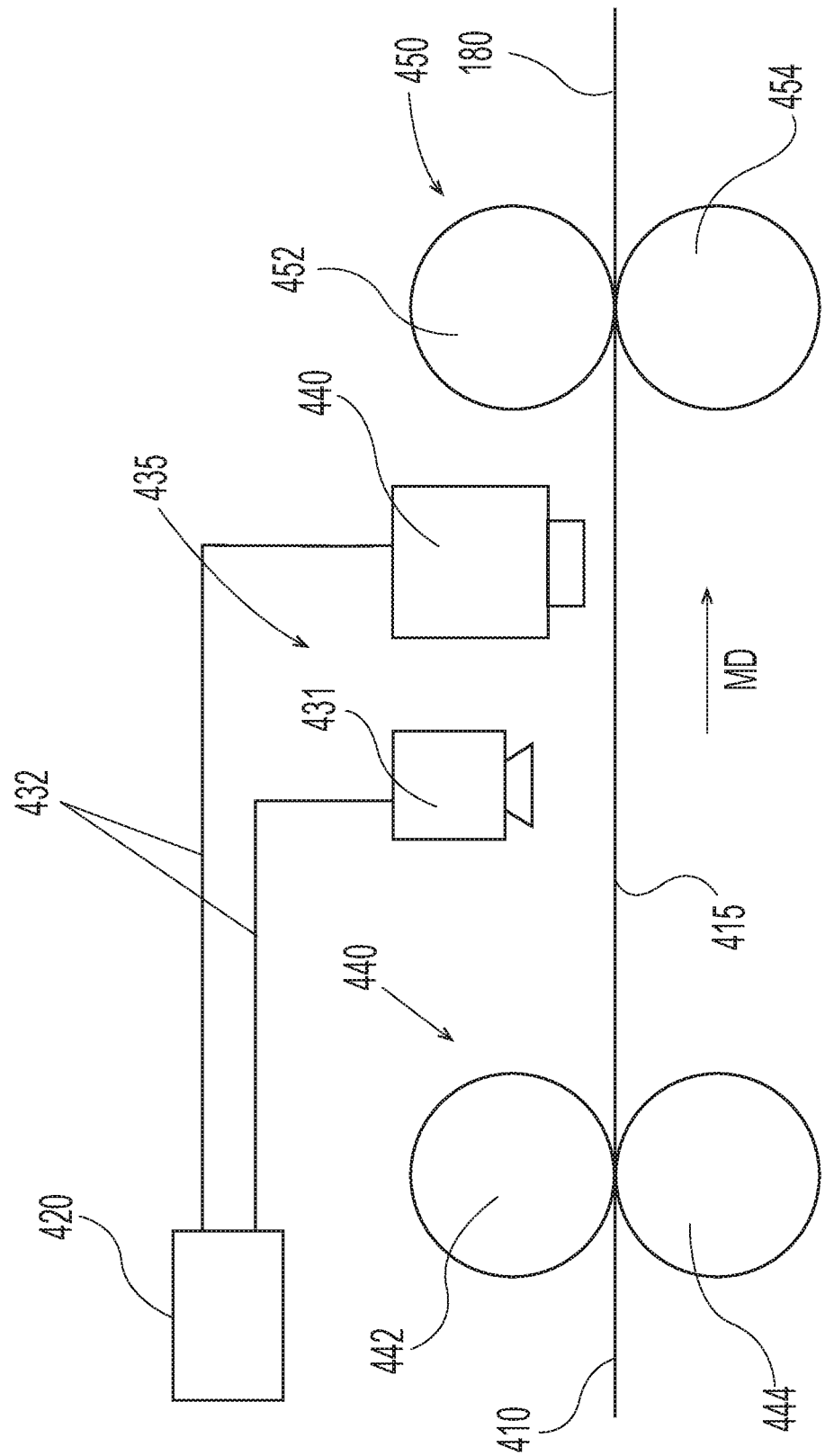
FIG. 4A is a schematic diagram showing a process in accordance with the present disclosure.

FIG. 4A depicts an exemplary process for carrying out a method of the present invention. The process shown in FIG. 4A allows for the deposition of one or more composition sites prior to the formation of an aperture in a web. As shown, a precursor web 410 may be provided to a first unit operation 440. As noted above, the precursor web 410 may comprise a nonwoven web, a film web, or a laminate created therefrom, e.g. nonwoven/nonwoven, film/film, nonwoven/film, or the like.

In some forms, the first unit operation 440 may comprise a patterned calendar roller 442 and a smooth anvil roller 444. One or both of the patterned calendar roller 442 and the smooth anvil roller 444 may be heated and the pressure between the two rollers may be adjusted by known techniques to provide the desired temperature, if any, and pressure to concurrently weaken and melt-stabilize (i.e., overbond) the precursor web 410 at a plurality of locations forming a plurality of intermediate features 411 (See FIG. 4B). At the first unit operation 440, the precursor web 410 is transformed into an intermediate web 415 (See FIG. 4B).

While FIG. 4A depicts a unit operation 440 which creates intermediate features 411 a web comprising intermediate features may be obtained from a supplier. For example, a manufacturer could obtain a web comprising melt stabilized areas, e.g. overbonds, provided by a web supplier. In such instances, the need for the first unit operation 440 would be reduced if not eliminated.

Still referring again to FIGS. 4A and 4B, the intermediate web 415 may pass through an inspection/print station 435. As shown, inspection/print station 435 may comprise a camera 431 which is in signal communication 432 with a computational device 420 and a printer 440 in signal communication with the computational device 420. An image captured by the camera 431 can vary. For example, the camera 431 can capture an image of a first group 411A of intermediate features 411. As another example, the camera 431 can capture an image(s) of the first group 411A, a second group 411B, and/or a third group 411C of intermediate features 411. In some forms, the camera 431 may capture an image of at least a portion of the first group 411A, second group 411B and/or third group 411C of intermediate features 411.

The camera 431 may transmit the image of the first group 411A, the second group 411B and/or the third group 411C, or at least a portion(s) thereof, to the computational device 420. The computational device 420 analyzes the transmitted image or images provided by the camera 431 to detect the intermediate features 411 of the submitted image(s) and determine where to print the composition. Additionally, if desired, the computational device may determine any phase shift between the intermediate features 411. The determination of phase shift of intermediate features is described in U.S. Patent Application Publication No. 2017/0225449.

Figure 4B:
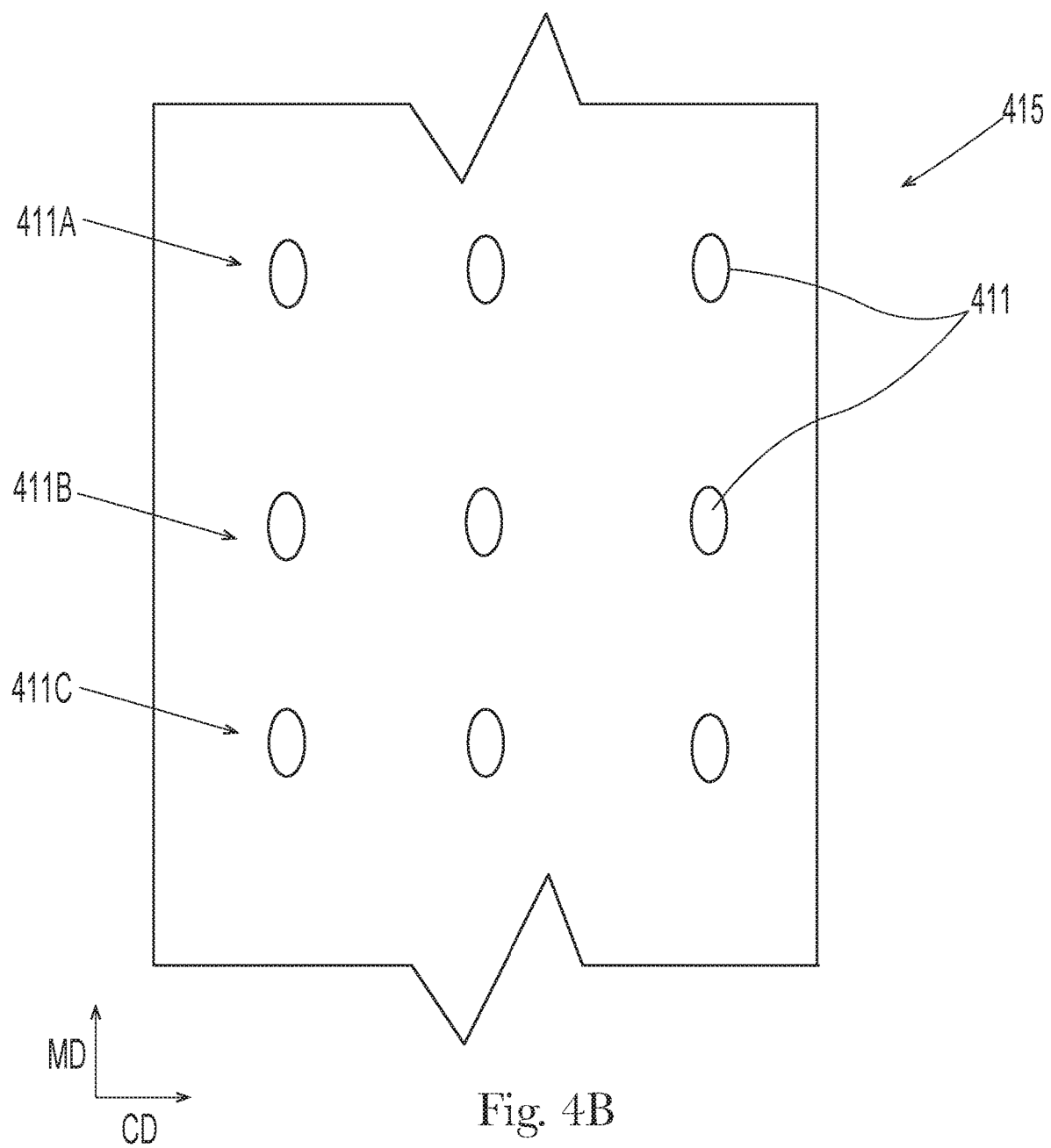
FIG. 4B is a plan view of an exemplary intermediate web constructed in accordance with the present disclosure.
Figure 4C:
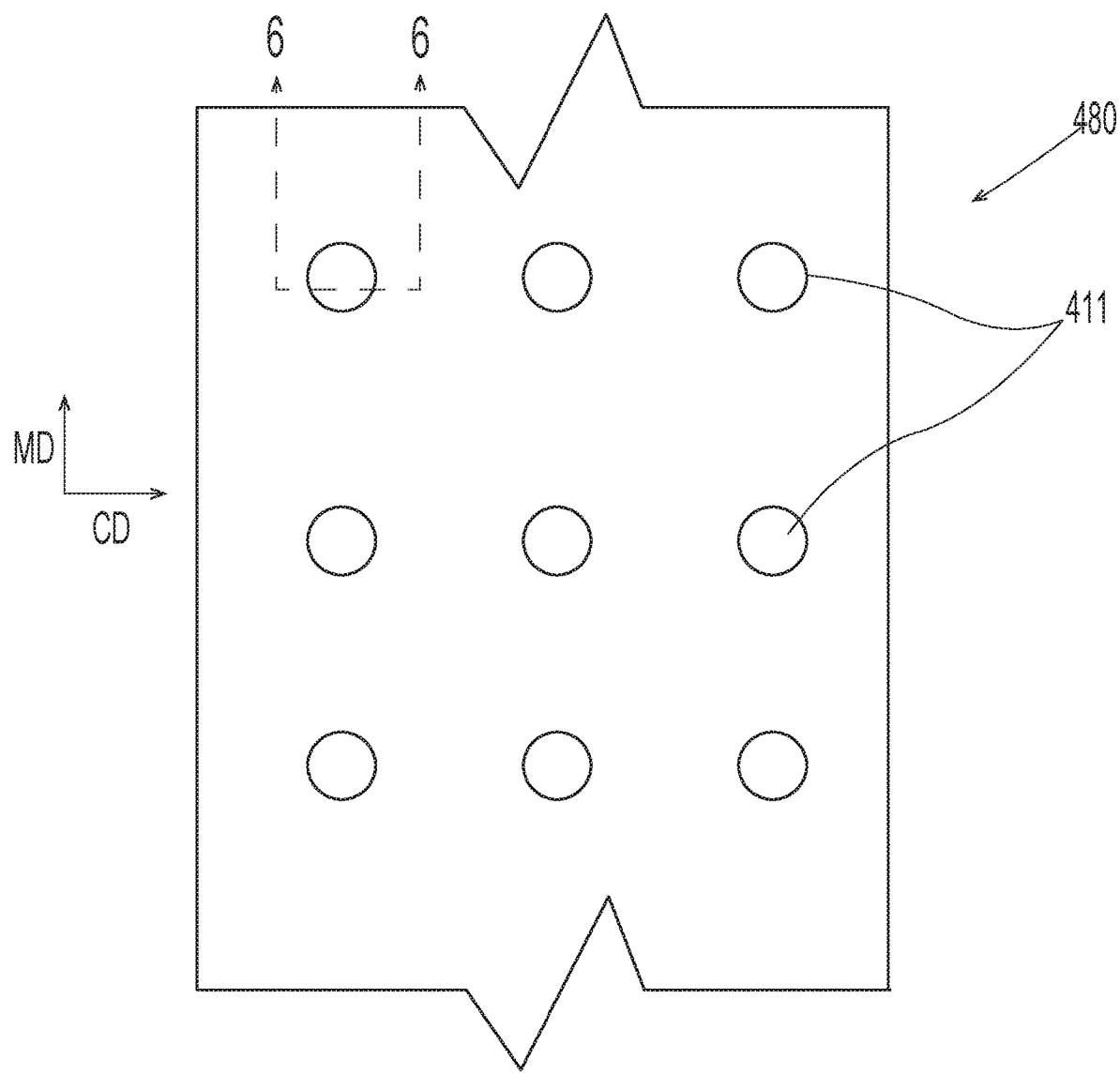
FIG. 4C is a plan view of an exemplary secondary web constructed in accordance with the present disclosure.

Referring to FIGS. 4A-4C, after the deposition of the composition(s) onto the intermediate web 415, the intermediate web 415 may experience a second unit operation 450 which transforms the intermediate features 411 into apertures 490. For example, the second unit operation 450 may comprise an incremental stretching system comprising two complimentary rolls 452 and 454 which intermesh with one another and stretch the intermediate web 415. The stretching of the intermediate web 415 can cause the intermediate features 411 to rupture/break apart into apertures 490 and form a secondary web 480.

Referring now to FIG. 5, the inspection/print station 435 may be provided in a variety of configurations. For example, the camera 431 may be positioned downstream of the printer 440. In such arrangements, the camera 431 may capture an image or images of the intermediate web 415 with the composition disposed thereon. In another example, the camera 431 may be positioned downstream of the second unit operation 450. In such configurations, the camera 431 can provide an image or images to the computational device 420. In such configurations however, detecting the composition on the intermediate web 415 and/or secondary web 480 (See FIGS. 4B and 4C, respectively) may require special lighting or excitation devices such that the composition can be highlighted in the image or images provided to the computational device 420. The inspection/print station 135 is discussed further hereafter.

In some forms of the present invention, the camera 431 may provide images directly to the printer 440. For example, as noted previously, the camera 431 may capture an image or image(s) with respect to the intermediate features and/or apertures. The camera 431 may then provide the image(s) directly to the printer 440 as a print file. The printer 440 may then apply compositions to the web in accordance with the image(s) provided by the camera 431. In such forms, the determination of the phase shift of the intermediate features 411 may not be required.

Suitable first and second unit operations forming intermediate features 411 and subsequently apertures 490 include those unit operations associated with stretch aperturing as described in U.S. Pat. Nos. 5,658,639; 5,628,097; 5,916,661; 7,917,985; and U.S. Patent Application Publication No. 2003/0021951. For such aperturing processes, referring to FIG. 6, in some forms, the composition sites 635 may comprise a first portion 635A disposed on side walls 495A and 495B of the aperture. Additionally, in some forms, the composition sites 635 may comprise a second portion 635B which is disposed on a first surface 485 of the secondary web 480. The first portion 635A and/or second portion 635B may comprise a plurality of dots or droplets of composition particularly where ink jet printing is utilized. As such, on a microscopic scale, the first portion 635A and/or second portion 635B may appear discontinuous; however, to the naked eye, the first portion 635A and/or second portion 635B may appear continuous. Additional configurations are discussed hereafter. Other stretch aperturing operations are contemplated and are discussed in additional detail in U.S. Patent Application Publication Nos. 2016/0167334; 2016/0129661; and 2016/0136014. In these particular stretch aperturing operations, arrays of apertures can be created forming a pattern or a plurality thereof.

Figure 7A:
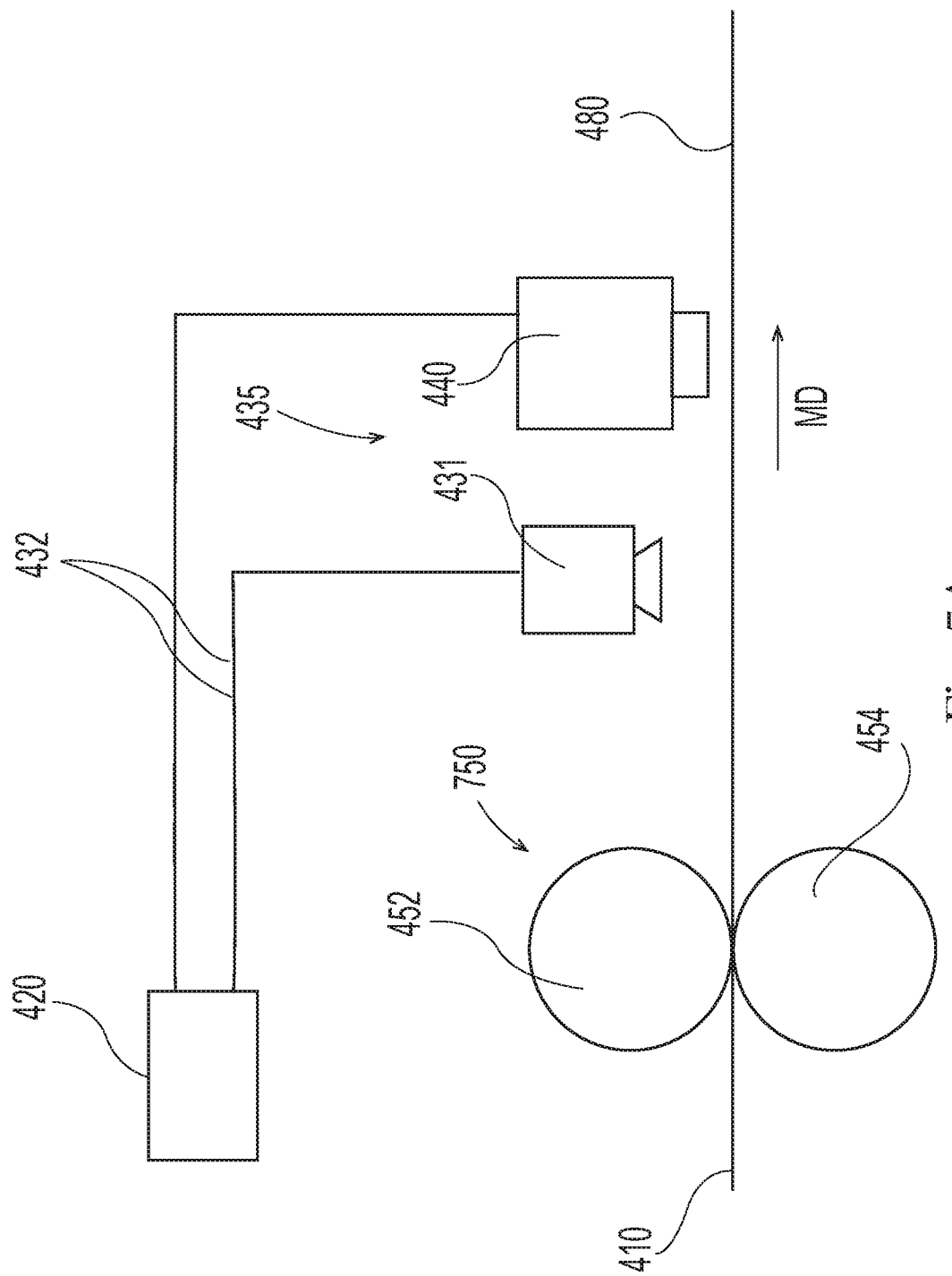
FIG. 7A is a schematic diagram showing a process in accordance with the present disclosure.
Figure 7B:
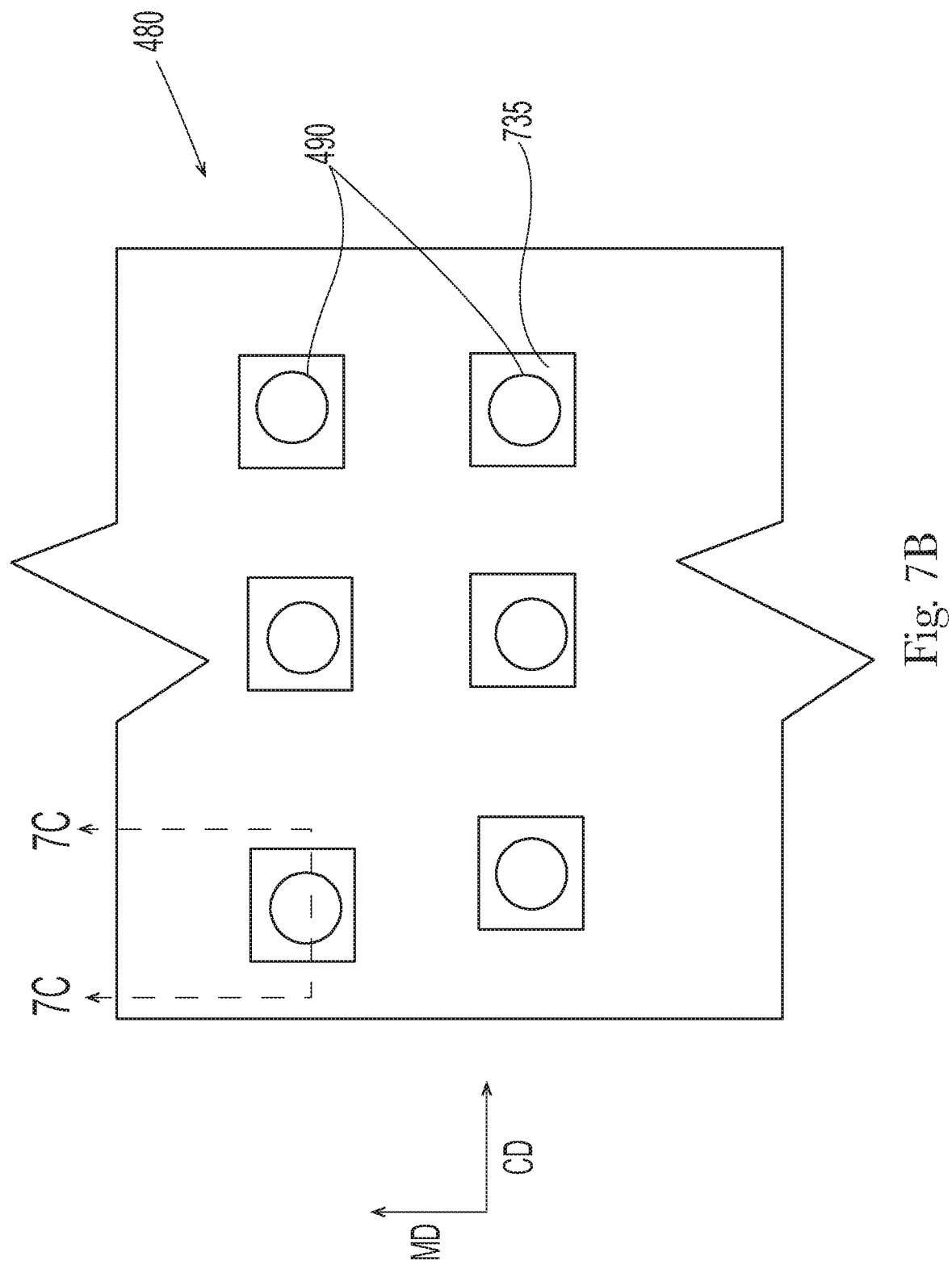
FIG. 7B is a plan view of an exemplary secondary web constructed in accordance with the present disclosure.

While FIG. 4A depicts two unit operations other configurations are contemplated. For example, only one unit operation may occur prior to the web passing through the visual inspection/print station 435. As shown in FIGS. 7A and 7B, a unit operation 750 may manipulate the precursor web 410 thereby producing a secondary web 780 with a plurality of apertures 490 (see FIG. 4C) therein. The visual inspection/print station 435 may be configured as previously described. For example, the printer 440 may be positioned upstream of the camera 431. The unit operation 750 may be configured similar to the second unit operation 450 described heretofore with regard to FIG. 4A.

As shown, dimensions and/or areas of a composition site 735 may be greater than dimensions and/or areas of the aperture 490. For example, a width of the composition sites 735 parallel to the CD can be greater than a width of the aperture 490 parallel to the CD. Similarly, a length of the composition sites 735 parallel to the MD may be greater than a length of the aperture 490 parallel to the MD. As noted previously, where a composition is registered with intermediate features, the composition sites may more closely match the dimensions of the resulting aperture. The length of the composition sites 735 may be greater than about 0.5 mm than the length of the aperture 490. Similarly, the width of the composition sites 735 may be greater than about 0.5 mm than the width of the aperture 490. In some forms, the length and/or width of the composition sites 735 may be greater than about 0.1 mm, greater than about 0.2 mm, greater than about 0.3 mm, greater than about 0.4 mm, greater than about 0.5 mm, greater than about 0.6 mm, greater than about 0.7 mm, greater than about 0.8 mm, greater than about 0.9 mm, or greater than about 1.0 mm than the width of the aperture, specifically including all values within each of the above and all ranges created thereby. The composition sites correlating to intermediate features may be sized similarly with regard to the intermediate feature(s).

Figure 7C:
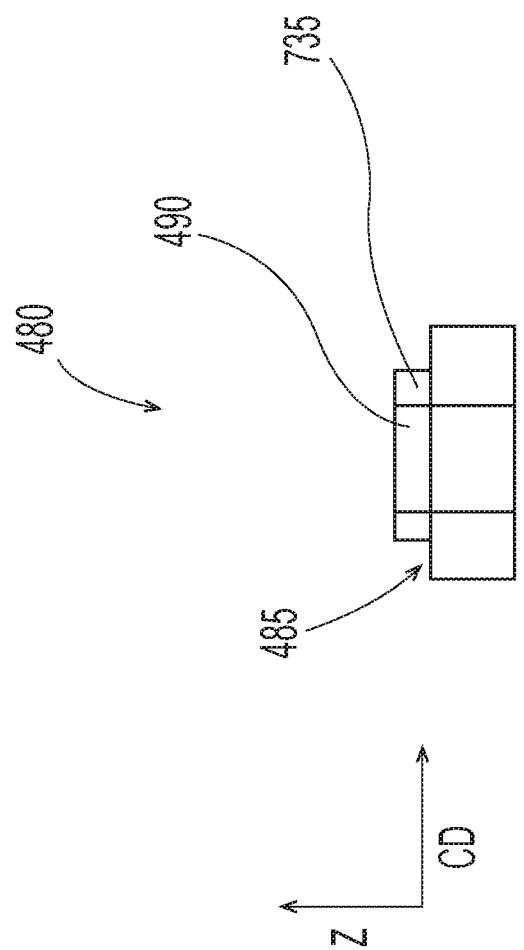
FIG. 7C is an exemplary cross section of the web shown in FIG. 7B constructed in accordance with the present disclosure.

In some forms, the width of the composition sites 735 may be greater than its length to accommodate period variability of the apertures 490. For those forms of the present invention where an intermediate feature is not provided, the composition sites 735 may be disposed on the first surface 485 of the secondary web 480 as shown in FIG. 7C. Some suitable processes for forming apertures without creating intermediate features may include those described in U.S. Pat. Nos. 8,679,391 and 8,158,043, and U.S. Patent Application Publication Nos. 2001/0024940 and 2012/0282436. Additional examples include hot pin, punching, die cutting, rotary knife aperturing, etc.

Figure 8A:
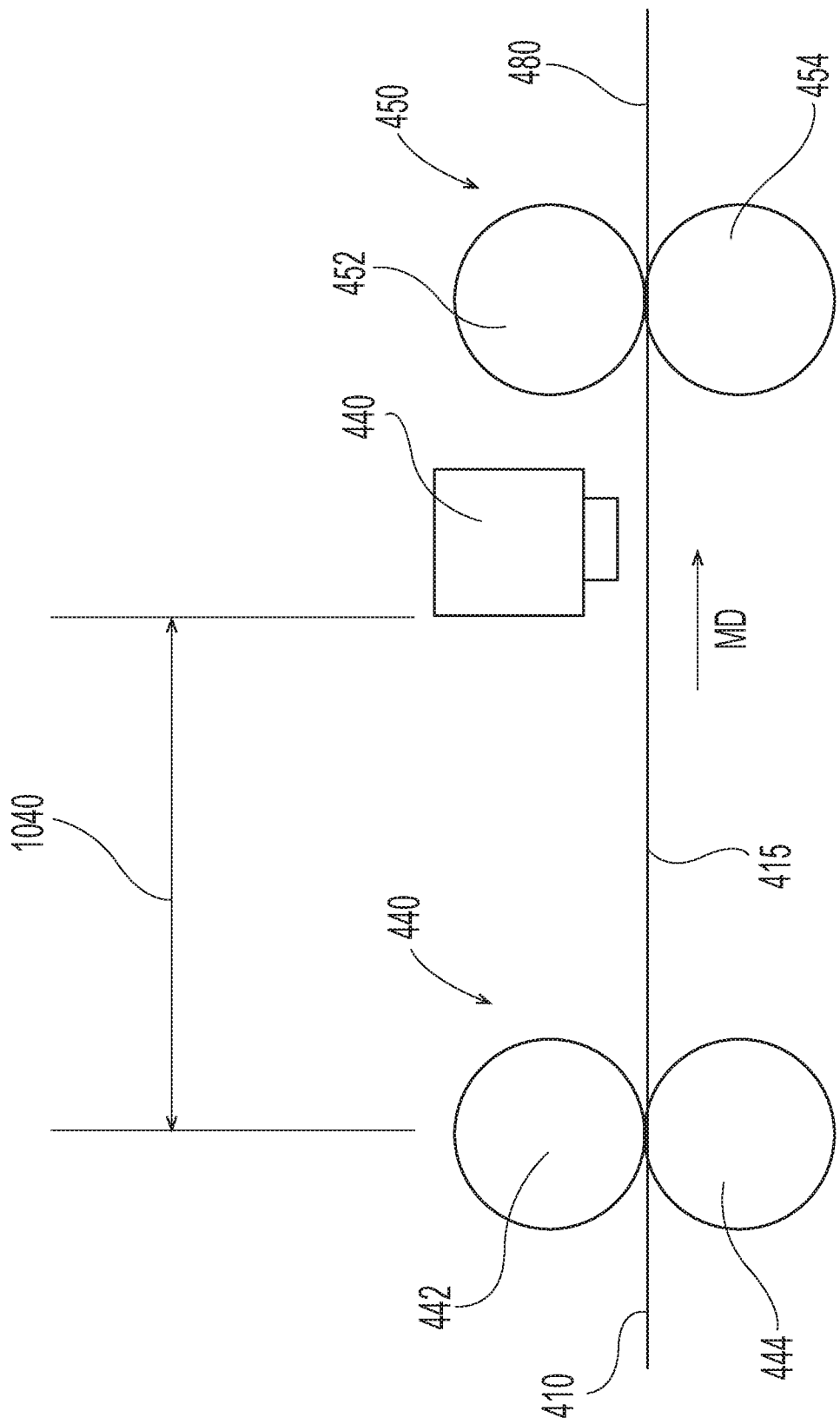
FIGS. 8A-8C are schematic diagrams showing processes in accordance with the present disclosure.

Addition processes are contemplated which do not utilize a visual system. Examples are provided with regard to FIGS. 8A-8C. In some forms of the present invention, compositions may be associated with intermediate features and/or aperture without the use of a vision system. For example, as shown in FIG. 8A, the printer 440 may be disposed between the first unit operation 440 and the second unit operation 450. If the printer 440 is positioned within a distance 1040 between the first unit operation 440 and the printer 440, the intermediate web 415 may track within such a small extent that a vision system is not needed. In such forms, the step of forming the intermediate features and printing is simply a matter of sequencing.

Figure 8B:
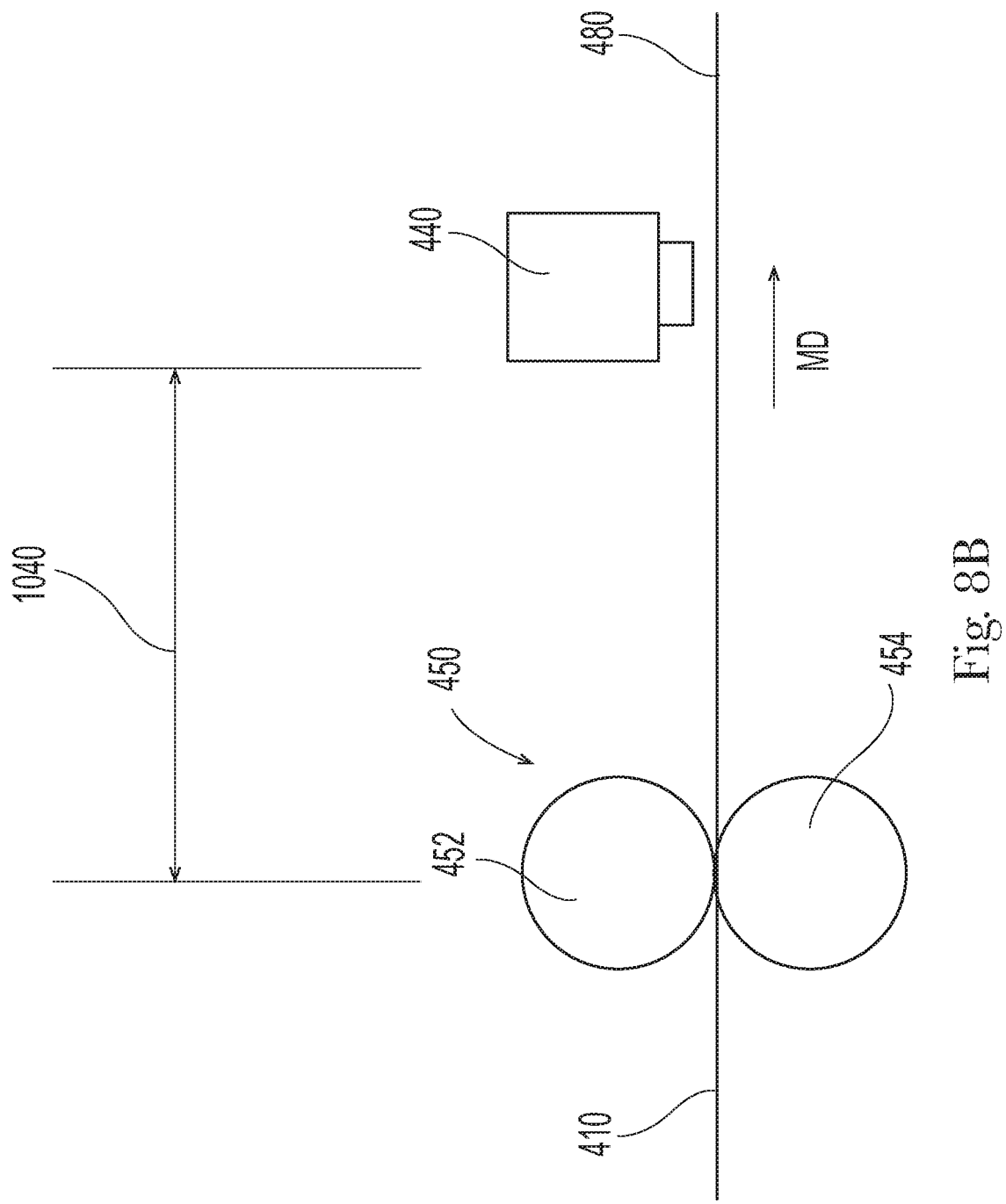
Figure 8C:
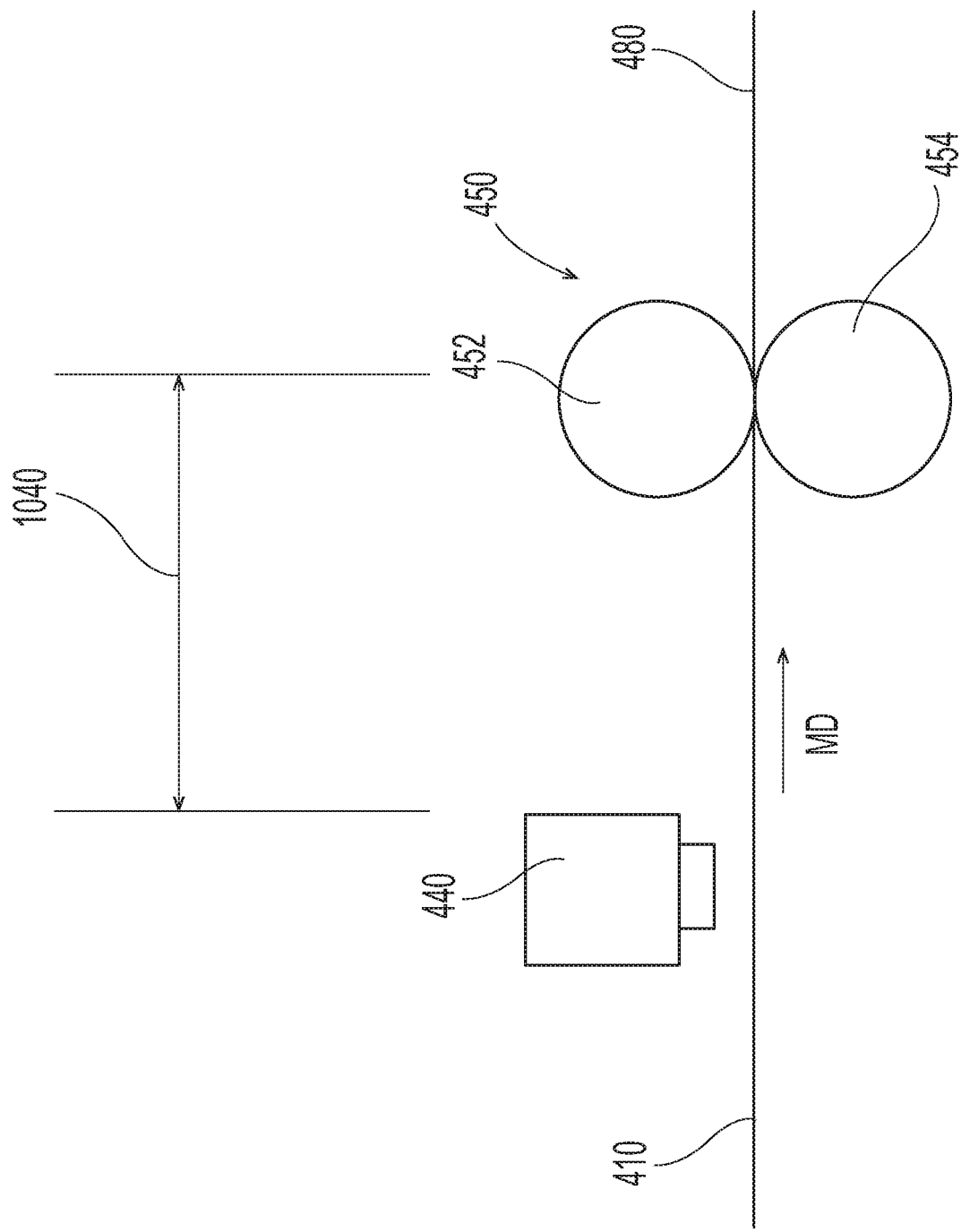

With regard to FIG. 8B, for those forms where a composition or composition(s) are applied to the web post formation of the apertures, the printer 440 may be positioned within a distance 1040 of the unit operation 450. Similarly, as shown in FIG. 8C, the printer 440 may be positioned within the distance 1040 upstream of the unit operation 450. In some forms of the present invention, the distance 1040 may be less than 5 times web width in the CD. In some forms, even where the distance 1040 is 5 times the web width in the CD or less, a vision system may still be utilized.

Depending on the manner in which the compositions are provided to the web, it is important to consider the rheology of the compositions being applied. For example, viscosity of the composition can be an important factor as viscosities which are too low can migrate out of the applied area, e.g. first composition sites. In contrast, a composition with too high of a viscosity can be difficult to apply via digital printer. And, other forms of application of the composition may prove to be much slower than that of the digital printer.

The composition of the present invention may be formulated to optimize its deposition by non-contact printing, e.g. ink jet printing. For example, the components of the desired composition can be dissolved or dispersed in a suitable solvent, such as water or another organic solvent. Some suitable organic solvents include ketones such as acetone, diethyl ketone, cyclohexanone and the like. Additional suitable solvents include alcohols such as methanol, ethanol, n-propanol, isopropanol, n-butanol, 1-methoxy-2-propanol, and the like. Additional suitable solvents include esters such as ethyl acetate, propyl acetate, butyl acetate and the like. Additional examples include ethers, lactones and amides. If desired, a mixture of solvents may be used. Additionally, surfactants, rheology modifiers, and colorants such as dyes or pigments may be added to the formulation. Moreover, the addition of heat to the composition may be utilized to provide an appropriate viscosity for the composition.

Inkjet printing generally relies on the generation of sequences of droplets. Behavior of the composition during droplet ejection is dependent on material properties such as density, viscosity and surface tension. The behavior of a composition when inkjet printed can be predicted via two dimensionless numbers, i.e. Ohnesorge number and Weber number. The equation for determining the Oh number is provided below.

$$Oh = \frac{\eta}{\sqrt{\rho \gamma L}}$$

where $\eta$ is viscosity, $\rho$ is density, $\gamma$ is surface tension of the composition, and L is the characteristic diameter (print head nozzle diameter for inkjet printing in meters).

Stable drop formation can be characterized by the reciprocal of the Ohnesorge number, namely Z=1/Oh. Stable drop formation can be expected from compositions when 14≥Z≥1. The viscosity of the desired composition should be measured at target operating temperature with shear rates between 200 and 20 s-1. The surface tension should be recorded in N/m. The density should be calculated in kg/m3, and the viscosity should be recorded in Pa·s.

Additionally, a composition of the present invention may comprise a Weber number of between about 4 and 1000. The Weber number may be calculated as follows:

$$We = \frac{v^2 \rho L}{\gamma}$$

where $\rho$ is the density of the composition in kg/m3; v is the velocity of the composition in m/s; L is the characteristic diameter (print head nozzle diameter for inkjet printing; and $\gamma$ is the surface tension in N/m.

The compositions of the present invention may comprise a viscosity of between about 5 and 25 centipoise. The compositions may comprise a surface tension of between about 25 and 40 dyne. In some forms of the present invention, the compositions may comprise a density of from about 0.6 grams/cubic cm to about 2.0 grams/cubic cm, specifically including all values within this range and any ranges created thereby.

Equipment

Any suitable camera may be utilized. For example, a camera having a bit depth of at least 8 may be utilized. In another example, a camera having a bit depth of at least 12 or at least 16 may be utilized. Cameras with higher bit depth can provide the computational device with much more numerical resolution allowing for better filtering of images by the computational device.

Any suitable computational device may be utilized with the present invention. Some suitable examples can include central processing units (CPU), graphical processing units (GPU), and/or field programmable gate arrays (FPGA). The processing power/speed of the computational device may vary depending on the speed of the manufacturing line of which images are being provided to the computational device. For example, faster line speeds may require additional processing power to ensure that the computational device can keep up with the images being provided by the camera. In some forms of the present invention, manufacturing line speeds can be greater than about 1 m/s, greater than about 3 m/s, greater than about 4 m/s, greater than about 5 m/s, greater than about 6 m/s, greater than about 7 m/s, greater than about 8 m/s, greater than about 9 m/s, greater than about 10 m/s, greater than about 11 m/s, greater than about 12 m/s, greater than about 13 m/s or greater than about 14 m/s specifically including all values within the above values and any ranges created thereby.

The computational device can comprise any suitable vision analysis software. Some suitable examples include National Instruments® Vision Development Module, MathWorks® Image Processing toolkit, OpenCV—open source computer vision library written in C++, or ImageJ. The vision analysis software can allow a user to extract a Fourier plane from the image provided by the camera and extract the phase plane from the image provided by the camera.

Depending on the web being analyzed, settings may need to be adjusted. For example, apertures may be difficult to discern in low basis weight nonwovens without adjustment to the filtering to reduce the noise of the image signal. However, less filtering may be required for the same size apertures in a higher basis weight nonwoven. Samples of the images to be analyzed can be used in test runs to hone the filter settings and produce a signal which can provide accurate results.

Similarly, samples may be utilized to determine the best highlighting method for the intermediate features and/or apertures. For example, backlighting may be used to highlight apertures. However, backlighting may not provide good results for highlighting melt stabilized areas—intermediate features—on the web. As such, depending on the intermediate features and/or apertures being detected, different highlighting mechanisms can be used to determine which highlighting system provides the best image and best resolution for the computational device.

In some specific forms, polarized backlighting may be utilized. For example, where intermediate features comprise melt stabilized areas, the highlighting method may require a polarized backlight in conjunction with an analyzer on the camera. The analyzer on the camera may be oriented at 90 degrees to the polarizer.

Where low basis weight nonwovens are utilized, conventional lighting may not provide sufficient distinction between apertures and/or melt stabilized areas and thin areas of the nonwoven. With polarized backlighting, apertures in low basis weight nonwovens may appear light where the remainder of the nonwoven appears dark and provide sufficient distinction between apertures and thin areas of a nonwoven. The use of polarized backlighting is discussed in additional detail in U.S. Patent Application Publication No. 2017/0227462.

Additional forms of the present invention are contemplated where contrasting color materials may be utilized to facilitate visualization of features by the vision system. For example, a nonwoven laminate comprising contrasting color layers may facilitate viewing of the intermediate features, e.g. melt stabilized area. Further examples of color enhancement of apertures is described in U.S. Patent Application Publication No. 2016/0278986.

As noted previously, the vision analysis software can allow analysis of an image via the Fourier and phase plane of the image. Additionally, the vision analysis software can allow for comparisons between predetermined patterns and images from the camera—pattern recognition. Where the periodicity of the intermediate features and/or apertures is too disparate, Fourier analysis may not be appropriate. In such instances, pattern recognition may provide more accurate results/more accurate instructions to the printer. A pattern or a plurality of patterns of intermediate features and/or apertures would need to be provided to the computational device and/or printer such that the comparison could be made between the transmitted image and the stored pattern(s).

Configurations are contemplated where the camera provides an image to the computational device which then creates a print file from the image. The print file can then be provided to the printer without the need for analysis. For example, the print file can account for any phase shift in the MD or CD. In this form, the need for predetermined patterns may be obviated.

Any suitable printer may be utilized with the present invention. As noted previously, the composition sites may comprise a plurality of discrete dots or droplets. The volume of the ink droplets can depend on the particular printing technology. By way of example, printing units that are VIDEOJET™ continuous ink jet printers can have ink drop volumes of about 240 pL and are delivered at relatively high drop velocities (e.g., about 13 m/s). Other printing technology (e.g. piezo drop on demand) can deliver ink drops having relatively small volumes, such as ink drops having a volume ranging from about 1 pL to about 24 pL and believed to be as high as about 80 pL in some forms. These drops are delivered at lower drop velocities (i.e., about ½ m/s) than continuous inkjet printing. Those skilled in the art know there are different inkjet technologies (e.g., continuous, piezo, thermal, valve) and different drop size ranges and different jet velocities. In general, smaller drop size infers that the CD dpi (resolution) is higher. The range 1-24 pL would equate to a CD resolution of 300-600 dpi. The VIDEOJET CD resolution is 128 dpi. So, more drops in CD can mean better opportunity to hit a fiber, which can result in better image quality and less ink blow-though. The slower the drop speed, the less ink blow-through.

An exemplary continuous ink jet printer is available from Videojet™ sold under the trade name of Videojet BX™. For the continuous ink jet printer, the ink droplets are dispensed from all of the jets of the print heads continuously, but only certain ink droplets are allowed to reach the precursor web, intermediate web, or secondary web, at the composition sites. The other ink droplets can be prevented from reaching the precursor web, intermediate web, or secondary web by deflecting the ink droplets into a recycling flow for a continuous re-use. The operation of the individual ink jets of each print head can be controlled by a controller included in the Videojet BX™ system.

Exemplary drop on demand printers for use in the present invention may comprise multiple print heads allowing for the deposition of a plurality of compositions. In general, the printer of the present invention may comprise a controller, one or more print heads, and a composition management system. A suitable example of a printer includes the 1024 PH development kit available from FujiFilm Dimatix™ located in New Hampshire. A suitable example of the print heads which may be utilized, includes SG-1024 MA available from FujiFilm Dimatix™. Forms of the present invention are contemplated where the controller 420 (See FIGS. 4A, 5 and 7) is utilized as the controller for the printer described above. Additional forms are contemplated where the printer described above comprises a separate controller in addition to the controller 420. Still in other forms of the present invention, where the need for a vision system is optional based upon the above disclosure, the controller for the printer may operate without the controller 420.

Another suitable printer is the Galaxy Phase Change Online Printer available from FujiFilm. Print heads for the Galaxy Phase Change online printer are available from Fujifilm Dimatix under the trade name Galaxy PH256/80HM. The advantage of using a heated print head, is that viscous liquids can be printed if the viscosity is reduced as temperature increases.

Disposable Absorbent Articles

The webs of the present invention may be processed to a further extent to create disposable absorbent article. Some suitable examples include diapers, diaper pants, feminine pads, adult incontinence pads, etc. The webs of the present invention may form any suitable portion of a disposable absorbent article. For example, the webs of the present invention may form a portion of a topsheet, a backsheet, or an absorbent core which is disposed between the toposheet and the backsheet. In some forms, the webs of the present invention may be utilized to form barrier cuffs for a disposable absorbent article. In other forms, the webs of the present invention may be form a portion of at least one or more of the topsheet, backsheet, secondary topsheet, acquisition layer, distribution layer, absorbent core dusting layer, backsheet, barrier cuff, wing of a sanitary pad, ear on a diaper, or the like.

Exemplary disposable absorbent articles are shown with regard to FIG. 9. With regard to FIG. 9 a cross sectional view of disposable absorbent article 1700 is shown. The disposable absorbent article 1700 may comprise a topsheet 1710, a backsheet 1730, and an absorbent core 1720 disposed therebetween. Optional features include, barrier cuffs, gasketing cuffs, wings, or the like.

Figure 10:
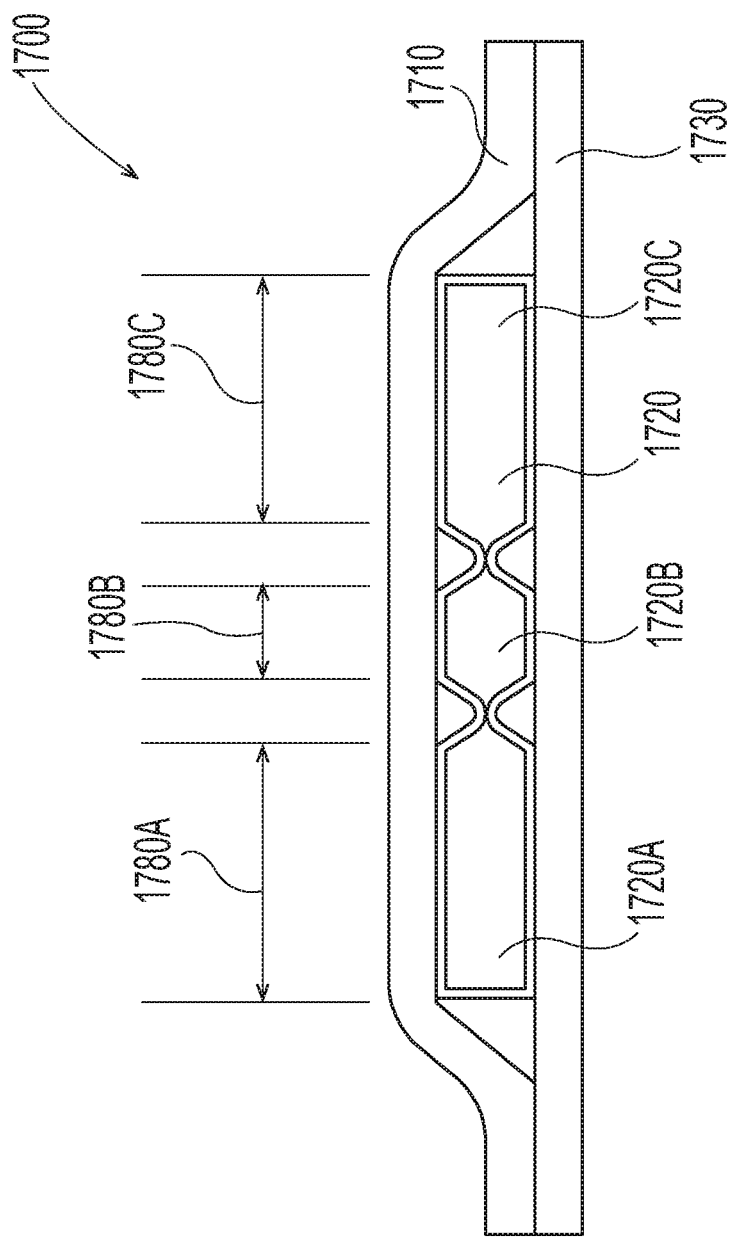
FIG. 10 is a schematic representation of a cross section of a disposable absorbent article constructed in accordance with the present disclosure.

Referring to FIG. 10, forms of the present invention are contemplated where the absorbent core 1720 comprises channels 1720A, 1720B, and 1720C. In such forms, a plurality of target zones 1780A, 1780B, and 170C, may exist, and each of the target zones may comprise a plurality of treated apertures and a plurality of untreated apertures, whereas apertures disposed between the target zones 1780A and 1780B and between 1780B and 1780C, may be untreated. In such forms, the target zones 1780A, 1780B, and 1780C may comprise a plurality of treated apertures and a plurality of untreated apertures.

For example, in some forms, less than about 75 percent of the apertures in the target zones 1780A, 1780B, and 1780C zone may be treated. In some forms, less than about 60 percent of the apertures in the target zones may be treated. In some forms, less than about 50 percent of the apertures in the target zones may be treated. In some forms, less than about 40 percent of the apertures in the target zones may be treated. In some forms, less than about 30 percent of the apertures in the target zones may be treated. In some forms, less than about 25 percent of the apertures in the target zones may be treated. In some forms, the percentage of treated apertures within the target zones may be between about 12 percent to about 75 percent, from about 20 percent to about 60 percent, or from about 25 percent to about 50 percent, specifically including all numbers within these ranges and any ranges created thereby.

The treated apertures within the target zones 1780A, 1780B, and 1780C may be configured such that the majority of treated aperture zones comprise more than one treated aperture. Or, these target zones may be configured such that the majority of treated aperture zones comprise only one treated aperture. Absorbent articles comprising absorbent cores having absorbent pockets may comprise a similar configuration with regard to the target zones and treated apertures/untreated apertures. Absorbent cores configured with channels are discussed in additional detail in U.S. Pat. No. 9,216,118. Absorbent cores configured with absorbent pockets are discussed in additional detail in U.S. Pat. No. 6,610,900. Absorbent cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The topsheet, backsheet, and/or absorbent core may comprise any suitable materials. Exemplary materials are disclosed in U.S. Patent Application Publication Nos. 2016/0167334A1; 2016/0129661A1; and 2016/0136014A1. Additionally, forms are contemplated where one or more fluid management layers are comprised by the absorbent article between the topsheet and the core and/or between the backsheet and the core, e.g. acquisition layers, distribution layers, secondary absorption layers, secondary topsheets, etc. Any suitable acquisition layer, distribution layer, secondary absorption layer, secondary topsheet and/or fluid management layer may be utilized.

Test Methods

Linear distances may be measured by any appropriate instrument that is calibrated and capable of a measurement to the nearest 0.1 mm. Area measurements are made using the projected area of the article, as viewed orthogonally to the plane of the longitudinal and transverse axes, in square millimeters to the nearest 0.1 mm$^2$.

Target Zone Test Method

The Target Zone Test Method is used to determine the target zone length index value and the transverse width of the target zone at multiple characteristic points.

A two-dimensional shape, defined by the projection of a planar absorbent article perpendicular to both its longitudinal and transverse axes, is captured and is hereafter referred to as the article projection. The article projection retains the same longitudinal and transverse axes of the article itself. The centroid of the article projection is calculated, and the position of the centroid along the longitudinal axis of the article projection is defined as the article centroid point. A line extending through the article centroid point and parallel to the transverse axis is used to partition the article projection into two sub-shapes, a first article projection and a second article projection. The centroids of the first article projection and second article projection are calculated and defined as the first centroid and second centroid, respectively. The position of the first centroid along the longitudinal axis of the article projection is defined as the first article centroid point. The position of the second centroid along the longitudinal axis of the article projection is defined as the second article centroid point.

Lines extending through the first and second centroid points parallel to the transverse axis of the article projection delineate the front and rear boundaries of the target zone. The length of the target zone along the longitudinal axis is calculated and reported to the nearest 0.1 mm.

The target zone length index value is calculated by dividing the length of the target zone by the total length of the core projection along the longitudinal axis and is a dimensionless ratio reported to the nearest 0.01.

The transverse width of the article projection is measured at the front centroid point and rear centroid point and each is reported to the nearest 0.1 mm. The transverse width of the article projection is measured at the narrowest point within the target zone and reported to the nearest 0.1 mm.

All measures are performed on five substantially similar absorbent cores and reported as the arithmetic mean of the five values.

Adjacent Treated Aperture Determination

Adjacency of treated apertures is determined using image analysis employing a Voronoi operation to generate a map of nearest neighbor apertures. Hydrophilic treated apertures are detected by briefly exposing a specimen to a colored water solution with subsequent imaging. The nearest neighbor map and treated aperture map are registered and compared to identify and connect adjacent treated apertures.

Sample Preparation

Test samples are conditioned at 23° C.±2° C. and 50%±2% relative humidity for 2 hours prior to testing and all testing is performed under these same environmental conditions. Remove the test article from its wrapper, if present, and make a mark on the top sheet about 3 mm inboard at each longitudinal end. Measure the distance between the two marks and record as the gage length to the nearest 1 mm. To obtain a test specimen, excise the entire top sheet from the article, taking care not impart any contamination or distortion to the layer during the process. A cryogenic spray (such as Quick-Freeze, Miller-Stephenson Company, Danbury, Conn.) can be used to remove the test specimen from the underlying layers if necessary.

Image Aquisition

Images of the top sheet, both initial and then after treatment detection, are collected as follows. The test specimen is suspended horizontally flat over a matte black background inside a light box that provides stable uniform lighting evenly across the entire base of the light box. A suitable light box is the Sanoto MK50 (Sanoto, Guangdong, China), or equivalent, which provides an illumination of 5500 LUX at a color temperature of 5500K. The illumination and color temperature are verified using a light meter prior to capturing images inside the light box to ensure the lighting conditions are consistent between each image obtained. A suitable light meter is the CL-70F CRI Illuminance Meter available from Konica Minolta, or equivalent. A Digital Single-Lens Reflex (DSLR) camera with manual setting controls (e.g. a Nikon D40X available from Nikon Inc., Tokyo, Japan, or equivalent) is mounted directly above an opening in the top of the light box so that the entire test specimen is visible within the camera's field of view.

Using a standard 18% gray card (e.g., Munsell 18% Reflectance (Gray) Neutral Patch/Kodak Gray Card R-27, available from X-Rite; Grand Rapids, Mich., or equivalent) the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of 1/400 sec. At a focal length of 35 mm the camera is mounted approximately 14 inches above the sample. The image is properly focused, captured, and saved as a JPEG file. The resulting image must contain the entire test specimen at a minimum resolution of 15 pixels/mm. The specimen image is distance calibrated against an image of a ruler (certified by NIST) acquired at the same focal length and resolution as the test specimen.

Obtain a total of 6 bars that are about 3 mm tall, no more than 25 mm wide and the length is similar to the width (lateral edge to lateral edge) of the test specimen. The bars are made of stainless steel (or equivalent) and heavy enough to sufficiently hold the test specimen in place. The test specimen is attached to two of the bars. Two bars will be used as risers in the dish of liquid and the other two bars will be used as risers in the light box.

Place the test specimen on a horizontally flat surface with the garment side facing up. Using double sided tape that is about 3 mm wide, secure the test specimen to the bottom surface of two bars immediately outboard of the two gage marks. Adjust the distance between the test specimen bars such that the distance between them is equal to the gage length. Place 2 risers on the matte white surface inside the light box such that the distance between them is equal to the gage length. Carefully transfer the test specimen to the light box and place the bars onto the risers, thereby suspending it horizontally flat over the matte white surface. Capture an image of the entire test specimen. This is the Initial Base Image (IBI). Remove the test specimen from the light box. Place a distance scale (certified by NIST) horizontally flat on top of the risers inside of the light box and capture an image at the same focal length and resolution as that used for the test specimen. This is the calibration image.

Detection of Treated Apertures

Prepare the test fluid by adding 0.05 wt % methylene blue dye (available from VWR International), or equivalent, to deionized water. Obtain a shallow dish large enough to allow the entire test specimen to lie horizontally flat inside. Place one riser at each end of the shallow dish such that the distance between them is equal to the gage length. Fill the dish with the colored test liquid to a depth equal to the height of the risers. Carefully transfer the test specimen to the dish of colored test liquid and place the bars onto the risers in the dish such that the body facing surface of the test specimen contacts the surface of the colored test liquid. Any hydrophilic areas on the test specimen will become notably colored (e.g. blue) within 10 seconds due to wetting by the colored test liquid. If a hydrophilic pattern is not detected, the test is over. After 10 seconds, if a hydrophilic pattern is detected, carefully transfer the test specimen (still attached to two bars) from the colored liquid to a sheet of blotting paper (e.g. Whatman grade 1, available from VWR International) that is the same size or larger than the test specimen. Allow the body facing surface of the test specimen to contact the blotting paper for no more than 3 seconds to remove any droplets of test liquid from the back surface. Carefully transfer the test specimen to the light box and place the bars onto the risers, thereby suspending it horizontally flat over a matte white surface. Collect an Treatment Detection Image (TDI) in like fashion as the IBI as described above.

Image Analysis

The calibration image file is opened in the image analysis program (e.g. Image J, distributed by the National Institute of Health, or equivalent). The resolution of the original image is resized to approximately 25 pixels per mm using bicubic interpolation. A linear distance calibration is performed using the imaged ruler. This distance calibration scale is applied to all subsequent specimen images prior to analysis. The Initial Base Image is opened a resized and calibrated consistent with the calibration image.

The image is then cropped to include only the test specimen and exclude the bars. Convert the image to 8-bit grayscale. The 8-bit grayscale image is then converted to a binary image (with "zero" or "black" corresponding to the aperture regions) in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-i} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined.

Two morphological operations are then performed on the binary image. First, a closing (a dilation operation, which converts any white background pixel that is touching (8-connected) a black pattern region pixel into a black pattern region pixel thereby adding a layer of pixels around the periphery of the pattern region, followed by an erosion operation, which removes any black pattern region pixel that is touching (8-connected) a white background pixel thereby removing a layer of pixels around the periphery of the pattern region, iterations=1, pixel count=1) is performed, which removes any background specks not associated to the pattern. Second, an opening (an erosion operation followed by a dilation operation, iterations=1, pixel count=1) is performed, which removes isolated black pixels. The edges of the image are padded during the erosion step to ensure that black boundary pixels are maintained during the operation.

Figure 11A:
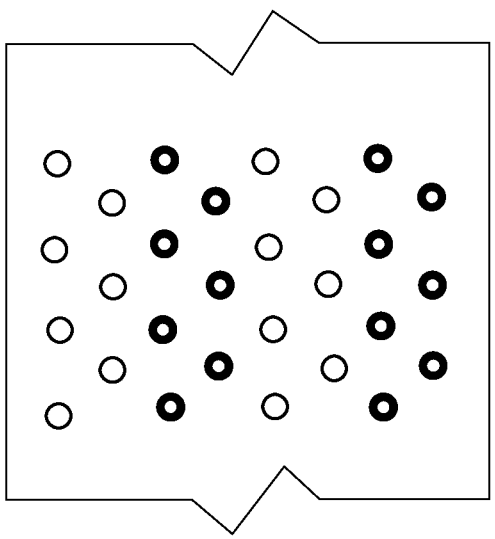
FIGS. 11A-11C are schematic illustrations showing zones of treated apertures.
Figure 11B:
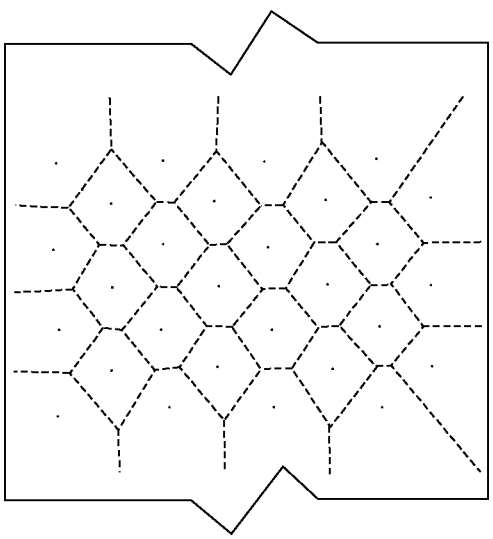

The apertures in the image are then eroded to find the single point representing the center of the aperture. Next a Voronoi operation is applied that generates a diagram of cells based on the aperture center point "seeds" (FIG. 11A-B).

Figure 11C:
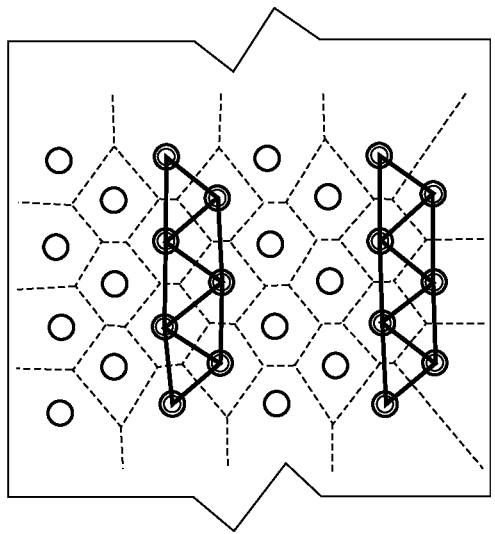

Using the Voronoi diagram generated from the Initial Base Image, map onto the cells the location of the treated apertures detected from the Treatment Detection Image. On the Voronoi diagram manually connect the treated apertures that are adjacent based on cells that have a planar interface between them (see FIG. 11C). Those cells with adjacent treated apertures are regions.

Contact Angle Method

Contact angles on substrates are determined using ASTM D7490-13 modified with the specifics as describe herein, using a goniometer and appropriate image analysis software (a suitable instrument is the FTA200, First Ten Angstroms, Portsmouth, Va., or equivalent) fitted with a 1 mL capacity, gas tight syringe with a No. 27 blunt tipped stainless steel needle. Two test fluids are used: Type II reagent water (distilled) in accordance with ASTM Specification D1193-99 and 99+% purity diiodomethane (both available from Sigma Aldrich, St. Louis, Mo.). All testing is to be performed at about 23° C.±2° C. and a relative humidity of about 50%±2%.

A 50 mm by 50 mm nonwoven substrate to be tested is removed from the article taking care to not touch the region of interest or otherwise contaminate the surface during harvesting or subsequent analysis. Condition the samples at about 23° C.±2° C. and a relative humidity of about 50%±2% for 2 hours prior to testing.

Set up the goniometer on a vibration-isolation table and level the stage according to the manufacturer's instructions. The video capture device must have an acquisition speed capable of capturing at least 10-20 images from the time the drop hits the surface of the specimen to the time it cannot be resolved from the specimen's surface. A capture rate of 900 images/sec is typical. Depending on the hydrophobicity/hydrophilicity of the specimen, the drop may or may not rapidly wet the surface of the nonwoven sample. In the case of slow acquisition, the images should be acquired until 2% of the volume of the drop is absorbed into the specimen. If the acquisition is extremely fast, the first resolved image should be used if the second image shows more than 2% volume loss.

Place the specimen on the goniometer's stage and adjust the hypodermic needle to the distance from the surface recommended by the instrument's manufacturer (typically 3 mm). If necessary adjust the position of the specimen to place the target site under the needle tip. Focus the video device such that a sharp image of the drop on the surface of the specimen can be captured. Start the image acquisition. Deposit a 5 µL±0.1 µL drop onto the specimen. If there is visible distortion of the drop shape due to movement, repeat at a different, but equivalent, target location. Make two angle measurements on the drop (one on each drop edge) from the image at which there is a 2% drop volume loss. If the contact angles on two edges are different by more than 4', the values should be excluded and the test repeated at an equivalent location on the specimen. Identify five additional equivalent sites on the specimen and repeat for a total of 6 measurements (12 angles). Calculate the arithmetic mean for this side of the specimen and report to the nearest 0.01°. In like fashion, measure the contact angle on the opposite side of the specimen for 6 drops (12 angles) and report separately to the nearest 0.01°.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article having a longitudinal centerline and a lateral centerline, the disposable absorbent article further comprising:
   a topsheet having a plurality of apertures, the plurality of apertures being arranged in a target zone, and a pair of outer zones, wherein the target zone comprises a primary target zone and a pair of secondary target zones positioned laterally outboard of the primary target zone, wherein between about 75% to about 100% of the plurality of apertures are treated with a treatment composition in the primary target zone, between about 25% to about 75% of the plurality of apertures are treated with a treatment composition in each of the secondary target zones, and at least a portion of the plurality of apertures in the outer zones are untreated;
   a backsheet attached to the topsheet; and
   an absorbent core disposed between the topsheet and the backsheet;
   wherein the topsheet comprises a first sub-layer and a second sub-layer; wherein the first sub-layer comprises fibers wherein the fibers comprise a hydrophobic melt additive; wherein at least a portion of the second sub-layer comprises a hydrophilic surfactant composition.

2. The disposable absorbent article of claim 1, wherein the target zone further comprises a pair of tertiary target zones positioned laterally outboard of the secondary target zones, wherein between about 12.5% to about 25% of the plurality of apertures are treated with a treatment composition in each of the tertiary target zones.

3. The disposable absorbent article of claim 1, wherein the pair of outer zones are positioned longitudinally outboard of the target zone.

4. The disposable absorbent article of claim 1, wherein the target zone extends a distance of from about 40% to about 80% of a total length of the absorbent article.

5. The disposable absorbent article of claim 1, wherein the absorbent article comprises a first lateral width and the target zone comprises a second lateral width, wherein the second lateral width is from about 50% to about 90% of the first lateral width.

6. The disposable absorbent article of claim 1, wherein the treatment composition is hydrophilic.

7. The disposable absorbent article of claim 1, wherein the treatment composition is a blood modifying agent.

8. The disposable absorbent article of claim 1, wherein the treatment composition is a lotion.

9. The disposable absorbent article of claim 1, wherein the treatment composition is applied to the web in a plurality of discrete dots.

* * * * *